US007867199B2

(12) United States Patent
Mogensen et al.

(10) Patent No.: US 7,867,199 B2
(45) Date of Patent: *Jan. 11, 2011

(54) INSERTER

(75) Inventors: Lasse Wesseltoft Mogensen, Søborg (DK); Magnus Walter Göransson, Malmø (SE)

(73) Assignee: Unomedical A/S, Birkeroed (DK)

( * ) Notice: Subject to any disclaimer, the term of this patent is extended or adjusted under 35 U.S.C. 154(b) by 931 days.

This patent is subject to a terminal disclaimer.

(21) Appl. No.: 11/298,259

(22) Filed: Dec. 9, 2005

(65) Prior Publication Data

US 2006/0161108 A1  Jul. 20, 2006

Related U.S. Application Data

(60) Provisional application No. 60/699,472, filed on Jul. 15, 2005, provisional application No. 60/679,453, filed on May 9, 2005, provisional application No. 60/634,940, filed on Dec. 10, 2004.

(51) Int. Cl.
*A61M 5/178* (2006.01)
(52) U.S. Cl. .............................. 604/164.04; 604/164.01
(58) Field of Classification Search ............ 604/164.04, 604/164.08, 164.12, 165.01, 288.01, 288.04, 604/181
See application file for complete search history.

(56) References Cited

U.S. PATENT DOCUMENTS

| 643,544 | A | 2/1900 | Simmons |
| 1,838,825 | A | 12/1931 | Goldstein |
| 1,991,103 | A | 2/1935 | King |
| 2,047,010 | A | 7/1936 | Dickinson |
| 2,295,849 | A | * | 9/1942 | Kayden .................. 604/136 |
| 2,319,731 | A | 5/1943 | Garrett |
| 2,533,731 | A | 12/1950 | Gomberg |
| 2,630,803 | A | 3/1953 | Baran |
| 2,690,529 | A | 9/1954 | Lindblad |
| 2,730,099 | A | 1/1956 | Sullivan |
| 2,839,060 | A | 6/1958 | Ormo |
| 2,936,141 | A | 5/1960 | Rapata |

(Continued)

FOREIGN PATENT DOCUMENTS

DE            893 296         12/1953

(Continued)

OTHER PUBLICATIONS

International Search Report from DK 200401914 dated Sep. 5, 2005.

(Continued)

*Primary Examiner*—Nicholas D Lucchesi
*Assistant Examiner*—Rebecca E Eisenberg
(74) *Attorney, Agent, or Firm*—Brinks Hofer Gilson & Lione

(57) ABSTRACT

The invention relates to an inserter for an infusion set for intermittent or continuous administration of a therapeutical substance such as e.g. insulin. The inserter comprises a needle unit comprising a needle hub and a carrier body, and a cannula housing. The cannula housing and the needle hub are releasably connected and when they are connected, the insertion needle is placed inside the cannula. The carrier body guides the movement relative to the set housing between a retracted and an advanced position. When released the needle unit and the cannula housing are forced by a spring unit to an advanced position where the needle and cannula are placed subcutaneously. One object of the invention is to provide a disposable inserter for an infusion set which inserter is easy and safe for the user to handle during use and to dispose of after use.

25 Claims, 23 Drawing Sheets

U.S. PATENT DOCUMENTS

| | | |
|---|---|---|
| 2,952,420 A | 9/1960 | Van Hoorn |
| 3,055,361 A | 9/1962 | Ballard |
| 3,074,541 A | 1/1963 | Roehr |
| 3,107,785 A | 10/1963 | Roehr |
| 3,154,080 A | 10/1964 | Rowan et al. |
| 3,317,166 A | 5/1967 | Janssen |
| 3,545,286 A | 12/1970 | Stenstrom |
| 3,610,240 A | 10/1971 | Harautuneian |
| 3,648,999 A | 3/1972 | Bauer |
| 3,783,996 A | 1/1974 | Gerard et al. |
| 3,814,097 A | 6/1974 | Ganderton et al. |
| 3,831,729 A | 8/1974 | Howard |
| 3,840,011 A | 10/1974 | Wright |
| 3,865,236 A | 2/1975 | Rycroft |
| 3,937,219 A | 2/1976 | Karakashian |
| 3,942,528 A | 3/1976 | Loeser |
| 3,986,508 A | 10/1976 | Barrington |
| 4,014,328 A | 3/1977 | Cluff et al. |
| 4,022,205 A | 5/1977 | Tenczar |
| 4,146,113 A | 3/1979 | Gavel |
| 4,150,798 A | 4/1979 | Aragon |
| 4,188,950 A | 2/1980 | Wardlaw |
| 4,201,406 A | 5/1980 | Dennehey et al. |
| 4,227,528 A | 10/1980 | Wardlaw |
| 4,267,836 A | 5/1981 | Whitney et al. |
| 4,306,705 A | 12/1981 | Svenson |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,365,630 A | 12/1982 | McFlarlane |
| 4,400,861 A | 8/1983 | Parker |
| 4,406,042 A | 9/1983 | McPhee |
| 4,458,344 A | 7/1984 | Coogler |
| 4,472,024 A | 9/1984 | Konomura et al. |
| 4,473,369 A | 9/1984 | Lueders et al. |
| 4,500,312 A | 2/1985 | McFarlane |
| 4,517,971 A | 5/1985 | Sorbonned |
| 4,530,695 A | 7/1985 | Phillips et al. |
| 4,531,686 A | 7/1985 | Shaw |
| 4,576,846 A | 3/1986 | Noel |
| 4,606,735 A | 8/1986 | Wilder et al. |
| 4,610,469 A | 9/1986 | Wolff-Mooij |
| 4,616,790 A | 10/1986 | Beltran |
| 4,619,349 A | 10/1986 | Braun |
| 4,635,683 A | 1/1987 | Nielsen |
| 4,637,404 A | 1/1987 | Gessman |
| 4,662,873 A | 5/1987 | Lash et al. |
| 4,682,702 A | 7/1987 | Gach |
| 4,713,059 A | 12/1987 | Bickelhaupt et al. |
| 4,734,092 A | 3/1988 | Millerd |
| 4,755,173 A | 7/1988 | Konopka et al. |
| 4,758,020 A | 7/1988 | Boyd |
| 4,800,629 A | 1/1989 | Ikeda |
| 4,802,638 A | 2/1989 | Burger et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,878,897 A | 11/1989 | Katzin |
| 4,890,608 A | 1/1990 | Steer |
| 4,895,570 A | 1/1990 | Larkin |
| D306,500 S | 3/1990 | Brahler |
| 4,913,369 A | 4/1990 | Lia et al. |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,978,338 A | 12/1990 | Melsky et al. |
| 4,982,842 A | 1/1991 | Hollister |
| 4,986,817 A | 1/1991 | Code |
| 4,994,045 A | 2/1991 | Ranford |
| 5,011,475 A | 4/1991 | Olsen |
| 5,024,662 A | 6/1991 | Menes et al. |
| 5,067,496 A | 11/1991 | Eisele |
| 5,077,872 A | 1/1992 | Guthammar |
| 5,083,757 A | 1/1992 | Barsky |
| 5,098,389 A | 3/1992 | Cappucci |
| 5,112,313 A | 5/1992 | Sallee |
| 5,116,319 A | 5/1992 | Van den Haak |
| 5,116,324 A | 5/1992 | Brierley et al. |
| 5,116,325 A | 5/1992 | Paterson |
| 5,121,751 A | 6/1992 | Panalletta |
| 5,134,593 A | 7/1992 | Logan et al. |
| 5,134,594 A | 7/1992 | Woo |
| 5,137,524 A | 8/1992 | Lynn et al. |
| 5,141,496 A | 8/1992 | Dalto et al. |
| 5,147,319 A | 9/1992 | Ishikawa et al. |
| 5,147,375 A | 9/1992 | Sullivan et al. |
| 5,161,681 A | 11/1992 | Kemp et al. |
| 5,163,915 A | 11/1992 | Holleron |
| 5,176,662 A | 1/1993 | Bartholomew et al. |
| 5,188,314 A | 2/1993 | Peters |
| 5,188,611 A | 2/1993 | Orgain |
| RE34,223 E | 4/1993 | Bonaldo |
| 5,222,947 A | 6/1993 | D'Amico |
| 5,232,454 A | 8/1993 | Hollister |
| 5,236,143 A | 8/1993 | Dragon |
| 5,240,199 A | 8/1993 | Peters |
| 5,248,301 A | 9/1993 | Koenig et al. |
| 5,256,149 A * | 10/1993 | Banik et al. ............ 604/164.01 |
| 5,256,152 A | 10/1993 | Marks |
| 5,257,980 A | 11/1993 | Van Antwerp et al. |
| 5,265,822 A | 11/1993 | Shober, Jr. et al. |
| 5,269,799 A | 12/1993 | Daniel |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,343,637 A | 9/1994 | Schindler |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,376,082 A | 12/1994 | Phelps |
| 5,380,067 A | 1/1995 | Turvill et al. |
| 5,384,174 A | 1/1995 | Ward et al. |
| 5,387,197 A | 2/1995 | Smith et al. |
| 5,388,931 A | 2/1995 | Carlson |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,433,307 A | 7/1995 | Jeppe |
| D362,718 S | 9/1995 | Deily et al. |
| 5,449,349 A | 9/1995 | Sallee et al. |
| 5,487,506 A | 1/1996 | Drummond et al. |
| 5,490,841 A | 2/1996 | Landis |
| 5,492,313 A | 2/1996 | Pan et al. |
| 5,505,709 A | 4/1996 | Funderburk et al. |
| 5,507,730 A | 4/1996 | Haber et al. |
| 5,519,167 A | 5/1996 | Kunimoto et al. |
| 5,520,654 A | 5/1996 | Wahlberg |
| 5,522,803 A | 6/1996 | Teisson-Simony |
| 5,533,974 A | 7/1996 | Gaba |

| | | | | | | |
|---|---|---|---|---|---|---|
| 5,540,709 | A | 7/1996 | Ramel | 6,193,694 | B1 | 2/2001 | Bell et al. |
| 5,545,143 | A | 8/1996 | Fischell | 6,219,574 | B1 | 4/2001 | Cormier et al. |
| 5,545,152 | A | 8/1996 | Funderburk et al. | 6,221,058 | B1 | 4/2001 | Kao et al. |
| 5,554,130 | A | 9/1996 | McDonald et al. | 6,248,093 | B1 | 6/2001 | Moberg |
| 5,558,650 | A | 9/1996 | McPhee | 6,293,925 | B1 | 9/2001 | Safabash et al. |
| 5,562,636 | A | 10/1996 | Utterberg | 6,302,866 | B1 | 10/2001 | Marggi |
| 5,584,813 | A | 12/1996 | Livingston et al. | 6,319,232 | B1 | 11/2001 | Kashmer |
| 5,591,188 | A | 1/1997 | Waisman | 6,322,535 | B1 | 11/2001 | Hitchins et al. |
| 5,599,309 | A | 2/1997 | Marshall et al. | 6,322,808 | B1 | 11/2001 | Trautman et al. |
| 5,599,315 | A | 2/1997 | McPhee | 6,334,856 | B1 | 1/2002 | Allen et al. |
| 5,599,318 | A | 2/1997 | Sweeney et al. | 6,355,021 | B1 | 3/2002 | Nielsen et al. |
| 5,628,765 | A | 5/1997 | Morita | 6,379,335 | B1 | 4/2002 | Rigon et al. |
| 5,643,214 | A | 7/1997 | Marshall | D456,692 | S | 5/2002 | Epstein |
| 5,643,216 | A | 7/1997 | White | 6,387,076 | B1 | 5/2002 | Van Landuyt |
| 5,643,220 | A | 7/1997 | Cosme | 6,387,078 | B1 | 5/2002 | Gillespie, III |
| 5,662,617 | A | 9/1997 | Odell et al. | 6,405,876 | B1 | 6/2002 | Seshimoto et al. |
| 5,665,071 | A | 9/1997 | Wyrick | 6,488,663 | B1 | 12/2002 | Steg |
| 5,665,075 | A | 9/1997 | Gyure et al. | 6,517,517 | B1 | 2/2003 | Farrugia et al. |
| 5,681,323 | A | 10/1997 | Arick | 6,520,938 | B1 | 2/2003 | Funderburk et al. |
| 5,695,476 | A | 12/1997 | Harris | D472,316 | S | 3/2003 | Douglas et al. |
| 5,704,920 | A | 1/1998 | Gyure | D472,630 | S | 4/2003 | Douglas et al. |
| 5,709,516 | A | 1/1998 | Peterson et al. | 6,572,586 | B1 | 6/2003 | Wojcik |
| 5,714,225 | A | 2/1998 | Hansen et al. | 6,579,267 | B2 | 6/2003 | Lynch et al. |
| 5,741,288 | A | 4/1998 | Rife | 6,582,397 | B2 | 6/2003 | Alesi et al. |
| 5,752,923 | A | 5/1998 | Terwilliger | 6,595,962 | B1 | 7/2003 | Perthu |
| 5,810,835 | A | 9/1998 | Ryan et al. | 6,607,509 | B2 | 8/2003 | Bobroff et al. |
| 5,820,598 | A | 10/1998 | Gazza et al. | 6,607,511 | B2 | 8/2003 | Halseth et al. |
| 5,827,236 | A | 10/1998 | Takahashi | 6,629,949 | B1 | 10/2003 | Douglas |
| D402,538 | S | 12/1998 | Wagter et al. | 6,645,182 | B1 | 11/2003 | Szabo |
| 5,843,001 | A | 12/1998 | Goldenberg | 6,659,982 | B2 | 12/2003 | Douglas et al. |
| 5,851,197 | A | 12/1998 | Marano et al. | 6,685,674 | B2 | 2/2004 | Douglas et al. |
| 5,858,001 | A | 1/1999 | Tsals et al. | 6,702,779 | B2 | 3/2004 | Connelly et al. |
| 5,865,806 | A | 2/1999 | Howell | 6,726,649 | B2 | 4/2004 | Swenson et al. |
| 5,873,540 | A | 2/1999 | Hardin | 6,736,797 | B1 | 5/2004 | Larsen et al. |
| 5,899,886 | A | 5/1999 | Cosme | 6,749,589 | B1 | 6/2004 | Douglas et al. |
| 5,911,705 | A | 6/1999 | Howell | 6,790,199 | B1 | 9/2004 | Gianakos |
| 5,913,846 | A | 6/1999 | Szabo | 6,805,686 | B1 | 10/2004 | Fathallah et al. |
| 5,915,640 | A | 6/1999 | Wagter et al. | 6,811,545 | B2 | 11/2004 | Vaillancourt |
| 5,916,199 | A | 6/1999 | Miles | 6,814,720 | B2 | 11/2004 | Olsen et al. |
| 5,919,167 | A | 7/1999 | Mulhauser et al. | 6,824,530 | B2 | 11/2004 | Wagner et al. |
| 5,925,032 | A | 7/1999 | Clements | 6,824,531 | B1 | 11/2004 | Zecha, Jr. et al. |
| 5,947,935 | A | 9/1999 | Rinehart et al. | 6,830,562 | B2 | 12/2004 | Mogensen et al. |
| 5,951,523 | A | 9/1999 | Osterlind et al. | 6,837,877 | B2 | 1/2005 | Zurcher |
| 5,954,643 | A | 9/1999 | VanAntwerp et al. | 6,840,922 | B2 | 1/2005 | Nielsen et al. |
| 5,957,892 | A | 9/1999 | Thorne | 6,880,701 | B2 | 4/2005 | Bergeron et al. |
| 5,968,011 | A | 10/1999 | Larsen et al. | 6,916,017 | B2 | 7/2005 | Noe |
| 5,975,120 | A | 11/1999 | Novosel | 6,923,791 | B2 | 8/2005 | Douglas |
| 5,980,488 | A | 11/1999 | Thorne | 6,926,694 | B2 | 8/2005 | Marano-Ford et al. |
| 5,980,506 | A | 11/1999 | Mathiasen | 6,939,331 | B2 | 9/2005 | Ohshima |
| 5,984,224 | A | 11/1999 | Yang | 6,949,084 | B2 | 9/2005 | Marggi et al. |
| 5,984,897 | A | 11/1999 | Peterson et al. | 6,960,193 | B2 | 11/2005 | Rosenberg |
| 5,992,787 | A | 11/1999 | Burke | 6,991,619 | B2 | 1/2006 | Marano-Ford et al. |
| D417,733 | S | 12/1999 | Howell et al. | 6,991,620 | B2 | 1/2006 | Marano-Ford et al. |
| 6,017,328 | A | 1/2000 | Fischell et al. | 7,022,108 | B2 | 4/2006 | Marano-Ford et al. |
| D421,119 | S | 2/2000 | Musgrave et al. | 2001/0004970 | A1 | 6/2001 | Hollister et al. |
| 6,024,727 | A | 2/2000 | Thorne et al. | 2001/0016714 | A1 | 8/2001 | Bell et al. |
| 6,039,629 | A | 3/2000 | Mitchell | 2001/0021827 | A1 | 9/2001 | Ferguson et al. |
| 6,042,570 | A | 3/2000 | Bell et al. | 2001/0039401 | A1 | 11/2001 | Ferguson et al. |
| 6,045,533 | A | 4/2000 | Kriesel et al. | 2001/0041875 | A1 | 11/2001 | Higuchi et al. |
| 6,050,976 | A | 4/2000 | Thorne et al. | 2002/0022855 | A1 | 2/2002 | Bobroff et al. |
| 6,056,718 | A | 5/2000 | Funderburk et al. | 2002/0068904 | A1 | 6/2002 | Pluth et al. |
| 6,074,371 | A | 6/2000 | Fischell | 2002/0072720 | A1 | 6/2002 | Hague et al. |
| 6,086,008 | A | 7/2000 | Gray et al. | 2002/0077599 | A1 | 6/2002 | Wojcik |
| 6,086,575 | A | 7/2000 | Mejslov | 2002/0082543 | A1 | 6/2002 | Park et al. |
| 6,090,068 | A | 7/2000 | Chanut | 2002/0107489 | A1 | 8/2002 | Lee |
| 6,093,172 | A | 7/2000 | Funderburk et al. | 2002/0111581 | A1 | 8/2002 | Sasso |
| 6,093,179 | A | 7/2000 | O'Hara et al. | 2002/0145073 | A1 | 10/2002 | Swanson |
| 6,099,503 | A | 8/2000 | Stardella | 2002/0156424 | A1 | 10/2002 | Suzuki et al. |
| 6,105,218 | A | 8/2000 | Reekie | 2002/0156427 | A1 | 10/2002 | Suzuki et al. |
| 6,120,482 | A | 9/2000 | Szabo | 2002/0161332 | A1 | 10/2002 | Ramey |
| 6,123,690 | A | 9/2000 | Mejslov | 2002/0169419 | A1 | 11/2002 | Steg |
| 6,132,755 | A | 10/2000 | Eicher et al. | 2002/0173748 | A1 | 11/2002 | McConnell et al. |
| 6,183,464 | B1 | 2/2001 | Sharp et al. | 2002/0183688 | A1 | 12/2002 | Lastovich et al. |

| | | | | | |
|---|---|---|---|---|---|
| 2002/0189688 A1 | 12/2002 | Roorda | 2006/0095003 A1 | 5/2006 | Marano-Ford et al. |
| 2002/0193737 A1 | 12/2002 | Popovsky | | | |
| 2002/0193744 A1 | 12/2002 | Alesi et al. | FOREIGN PATENT DOCUMENTS | | |
| 2003/0060781 A1 | 3/2003 | Mogensen et al. | DE | 1 053 541 | 3/1959 |
| 2003/0069548 A1 | 4/2003 | Connelly et al. | DE | 26 20 009 A1 | 12/1977 |
| 2003/0105430 A1 | 6/2003 | Lavi et al. | DE | 28 03 509 A | 8/1979 |
| 2003/0109829 A1 | 6/2003 | Mogensen et al. | DE | 37 15 965 A | 1/1988 |
| 2003/0125669 A1 | 7/2003 | Safabash et al. | DE | 196 31 921 | 3/1997 |
| 2003/0125678 A1 | 7/2003 | Swenson et al. | DE | 298 18 311 U1 | 3/1999 |
| 2003/0130619 A1 | 7/2003 | Safabash et al. | DE | 19847143 A1 | 1/2000 |
| 2003/0139704 A1 | 7/2003 | Lin | DE | 101 06 074 A1 | 9/2000 |
| 2003/0158520 A1 | 8/2003 | Safabash et al. | DE | 299 21 406 U1 | 11/2001 |
| 2003/0176843 A1 | 9/2003 | Wilkinson | DE | 101 06 074 A1 | 6/2002 |
| 2003/0181863 A1 | 9/2003 | Davis et al. | DE | 203 20 207 U1 | 11/2004 |
| 2003/0181868 A1 | 9/2003 | Swenson | DK | 37 22 893 C1 | 6/1988 |
| 2003/0181873 A1 | 9/2003 | Swenson | DK | 38 23 447 | 2/1996 |
| 2003/0181874 A1 | 9/2003 | Bressler et al. | DK | 196 10 692 A1 | 9/1997 |
| 2003/0187394 A1 | 10/2003 | Wilkinson et al. | DK | 100 49 001 A1 | 4/2002 |
| 2003/0187395 A1 | 10/2003 | Wilkinson et al. | EP | 0 188 014 B1 | 10/1985 |
| 2003/0199823 A1 | 10/2003 | Bobroff et al. | EP | 0 239 244 B1 | 2/1987 |
| 2003/0216686 A1 | 11/2003 | Lynch et al. | EP | 0 298 521 B1 | 9/1990 |
| 2003/0225373 A1 | 12/2003 | Bobroff et al. | EP | 0 184 231 B1 | 1/1992 |
| 2003/0225374 A1 | 12/2003 | Mathiasen | EP | 0 475 857 | 3/1992 |
| 2003/0229308 A1 | 12/2003 | Tsals et al. | EP | 0 544 837 B1 | 6/1993 |
| 2003/0229316 A1 | 12/2003 | Hwang et al. | EP | 0 633 039 | 7/1994 |
| 2004/0002682 A1 | 1/2004 | Kovelman et al. | EP | 0 651 662 B1 | 5/1995 |
| 2004/0006316 A1 | 1/2004 | Patton | EP | 0 657 184 A1 | 6/1995 |
| 2004/0026840 A1 | 2/2004 | Eckel et al. | EP | 0 714 631 B1 | 6/1996 |
| 2004/0044306 A1 | 3/2004 | Lynch et al. | EP | 744 183 A2 | 11/1996 |
| 2004/0049159 A1 | 3/2004 | Barrus et al. | EP | 0 747 006 A1 | 12/1996 |
| 2004/0068231 A1 | 4/2004 | Blondeau | EP | 0 688 232 B1 | 12/1998 |
| 2004/0087913 A1 | 5/2004 | Rogers et al. | EP | 0 884 108 A1 | 12/1998 |
| 2004/0111068 A1 | 6/2004 | Swenson | EP | 0 916 361 A1 | 5/1999 |
| 2004/0112781 A1 | 6/2004 | Hofverberg et al. | EP | 0 931 560 A1 | 7/1999 |
| 2004/0116865 A1 | 6/2004 | Bengtsson | EP | 0 956 879 A1 | 11/1999 |
| 2004/0138612 A1 | 7/2004 | Shermer et al. | EP | 1 045 145 A1 | 10/2000 |
| 2004/0138620 A1 | 7/2004 | Douglas et al. | EP | 1 060 757 A1 | 12/2000 |
| 2004/0143216 A1 | 7/2004 | Douglas et al. | EP | 1 086 718 A | 3/2001 |
| 2004/0143218 A1 | 7/2004 | Das | EP | 1 125 593 A1 | 8/2001 |
| 2004/0158202 A1 | 8/2004 | Jensen | EP | 1 167 765 A2 | 1/2002 |
| 2004/0158207 A1 | 8/2004 | Hunn et al. | EP | 0 775 501 | 6/2002 |
| 2004/0162518 A1 | 8/2004 | Connelly et al. | EP | 0 894 216 B1 | 7/2003 |
| 2004/0171989 A1 | 9/2004 | Horner et al. | EP | 1 360 970 A1 | 11/2003 |
| 2004/0178098 A1 | 9/2004 | Swenson et al. | EP | 1 380 315 A1 | 1/2004 |
| 2004/0186446 A1 | 9/2004 | Ohshima | EP | 0 956 879 A1 | 7/2004 |
| 2004/0199123 A1 | 10/2004 | Nielsen | EP | 1 475 113 A | 11/2004 |
| 2004/0204687 A1 | 10/2004 | Mogensen et al. | FR | 576849 | 8/1924 |
| 2004/0204690 A1 | 10/2004 | Yashiro et al. | FR | 2 611 013 | 8/1988 |
| 2004/0220528 A1 | 11/2004 | Garcia, Jr. | FR | 2725902 | 10/1994 |
| 2004/0238392 A1 | 12/2004 | Peterson et al. | FR | 2733915 A1 | 11/1996 |
| 2004/0243065 A1 | 12/2004 | McConnell et al. | FR | 2781617 A1 | 1/2000 |
| 2004/0254433 A1* | 12/2004 | Bandis et al. ............... 600/347 | GB | 478803 | 1/1938 |
| 2004/0260235 A1 | 12/2004 | Douglas | GB | 591730 | 3/1946 |
| 2004/0260250 A1 | 12/2004 | Harris et al. | GB | 906574 | 9/1962 |
| 2005/0035014 A1 | 2/2005 | Cane | GB | 1 268 575 | 3/1972 |
| 2005/0101912 A1 | 5/2005 | Faust et al. | GB | 1 403 034 | 8/1975 |
| 2005/0101932 A1 | 5/2005 | Cote et al. | GB | 2 088 215 A | 6/1982 |
| 2005/0101933 A1 | 5/2005 | Marrs et al. | GB | 2 224 808 A | 5/1990 |
| 2005/0107743 A1 | 5/2005 | Fangrow, Jr. | GB | 2 270 552 A | 3/1994 |
| 2005/0113761 A1 | 5/2005 | Faust et al. | JP | 03-191965 A | 8/1991 |
| 2005/0119637 A1 | 6/2005 | Lundgren et al. | JP | 5326062 A | 12/1993 |
| 2005/0124936 A1 | 6/2005 | Mogensen et al. | JP | 7051251 | 11/1995 |
| 2005/0131347 A1 | 6/2005 | Marano-Ford et al. | JP | 08-187286 A | 7/1996 |
| 2005/0159709 A1 | 7/2005 | Wilkinson | JP | 9217584 A | 9/1997 |
| 2005/0215979 A1 | 9/2005 | Kornerup et al. | JP | 10-179734 A | 7/1998 |
| 2005/0251098 A1 | 11/2005 | Wyss et al. | JP | 2000-59877 A | 2/2000 |
| 2005/0277892 A1 | 12/2005 | Chen | JP | 2000059877 A | 2/2000 |
| 2005/0283114 A1* | 12/2005 | Bresina et al. ............ 604/93.01 | JP | 3140740 B2 | 3/2001 |
| 2006/0030815 A1 | 2/2006 | Csincsura et al. | JP | 2002-028246 | 1/2002 |
| | | | NL | 1017427 C | 11/2002 |
| | | | WO | WO 81/01795 A1 | 7/1981 |
| | | | WO | WO 82/03558 A1 | 10/1982 |

| | | | | | | |
|---|---|---|---|---|---|---|
| WO | WO 87/06474 | 11/1987 | | WO | WO 01/72353 A2 | 10/2001 |
| WO | WO 9204062 A1 | 3/1992 | | WO | WO 01/81785 A1 | 11/2001 |
| WO | WO 93/03787 | 3/1993 | | WO | WO 01/93926 A2 | 12/2001 |
| WO | WO 93/05840 | 4/1993 | | WO | WO 02/46080 | 6/2002 |
| WO | WO 94/20160 | 9/1994 | | WO | WO 02/066854 A1 | 8/2002 |
| WO | WO 95/28327 A | 10/1995 | | WO | WO 02/094352 | 11/2002 |
| WO | WO 96/20021 A1 | 7/1996 | | WO | WO 02/100457 | 12/2002 |
| WO | WO 96/35472 A1 | 11/1996 | | WO | WO 02/068014 | 1/2003 |
| WO | WO 98/09065 | 3/1998 | | WO | WO 03/015860 A1 | 2/2003 |
| WO | WO 98/58693 | 12/1998 | | WO | WO 03/026728 | 4/2003 |
| WO | WO 99/07435 | 2/1999 | | WO | WO 2004/030726 A | 4/2004 |
| WO | WO 99/33504 | 7/1999 | | WO | WO 2004/087240 | 10/2004 |
| WO | WO 99/36009 | 7/1999 | | WO | WO 2005/004973 | 1/2005 |
| WO | WO 99/56802 | 11/1999 | | WO | WO 2005/046780 A1 | 5/2005 |
| WO | WO 99/61815 | 12/1999 | | WO | WO 2005/068006 A1 | 7/2005 |
| WO | WO 00/02614 | 1/2000 | | | | |
| WO | WO 00/03757 | 1/2000 | | | | |
| WO | WO 00/44324 A1 | 8/2000 | | | | |
| WO | WO 01/04507 A1 | 1/2001 | | | | |
| WO | WO 01/30419 A2 | 5/2001 | | | | |
| WO | WO 01/68180 | 9/2001 | | | | |

OTHER PUBLICATIONS

Office Action mailed Apr. 1, 2010 for U.S. Appl. No. 11/721,263.

* cited by examiner

Fig. 15A
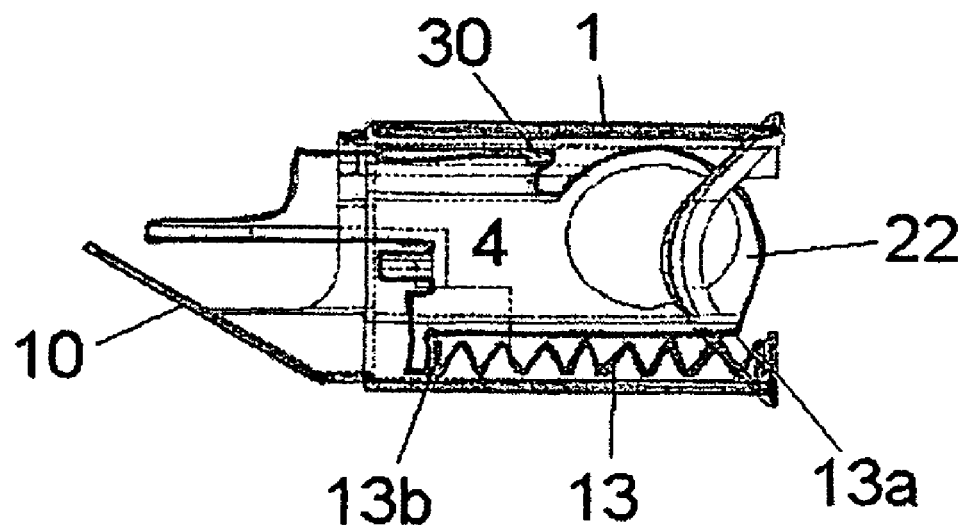
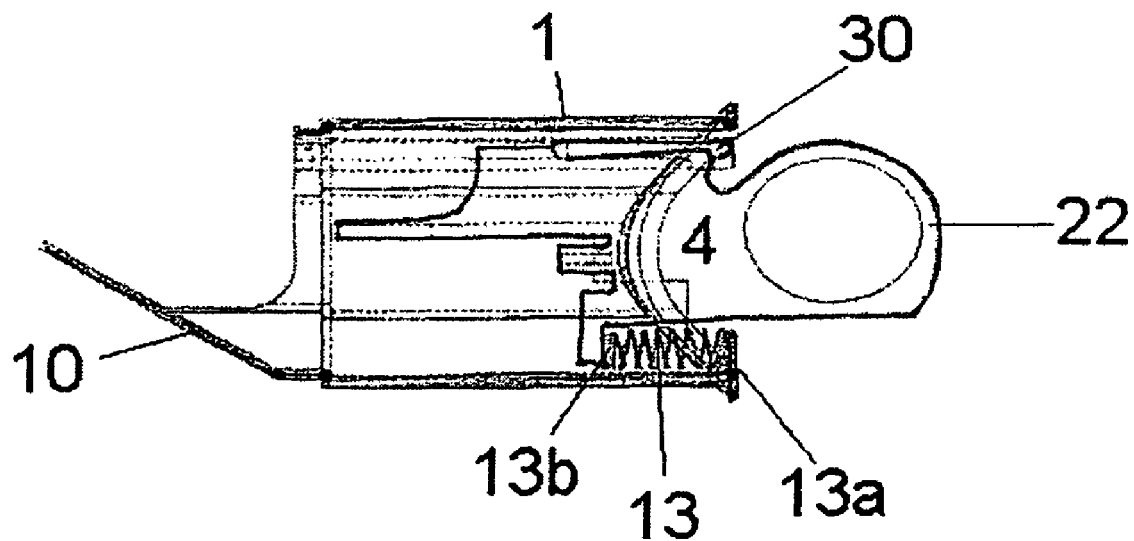
Fig. 15B

Fig. 17A
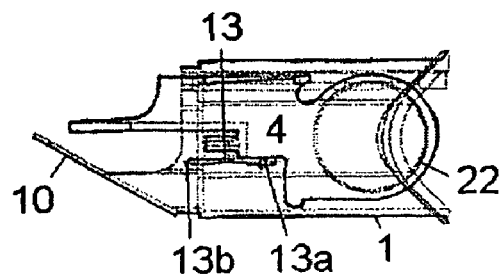
Fig. 17B
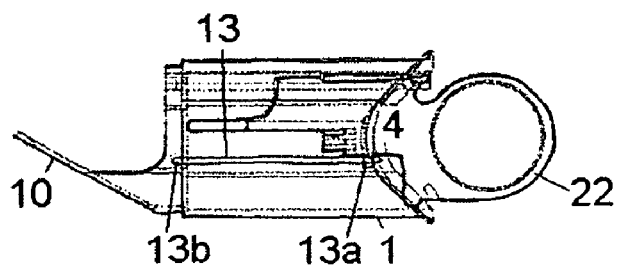
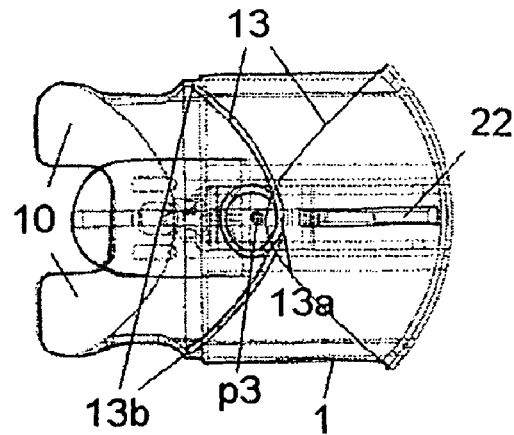
Fig. 17C
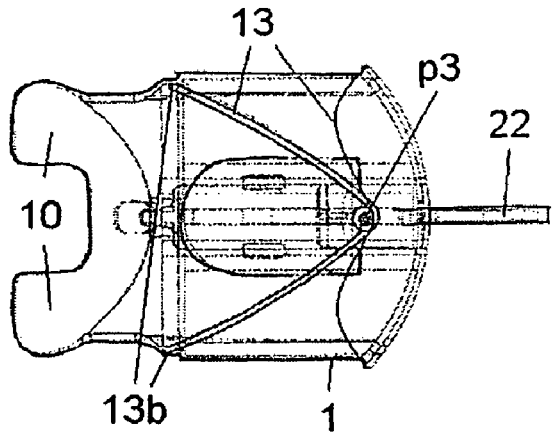
Fig. 17D

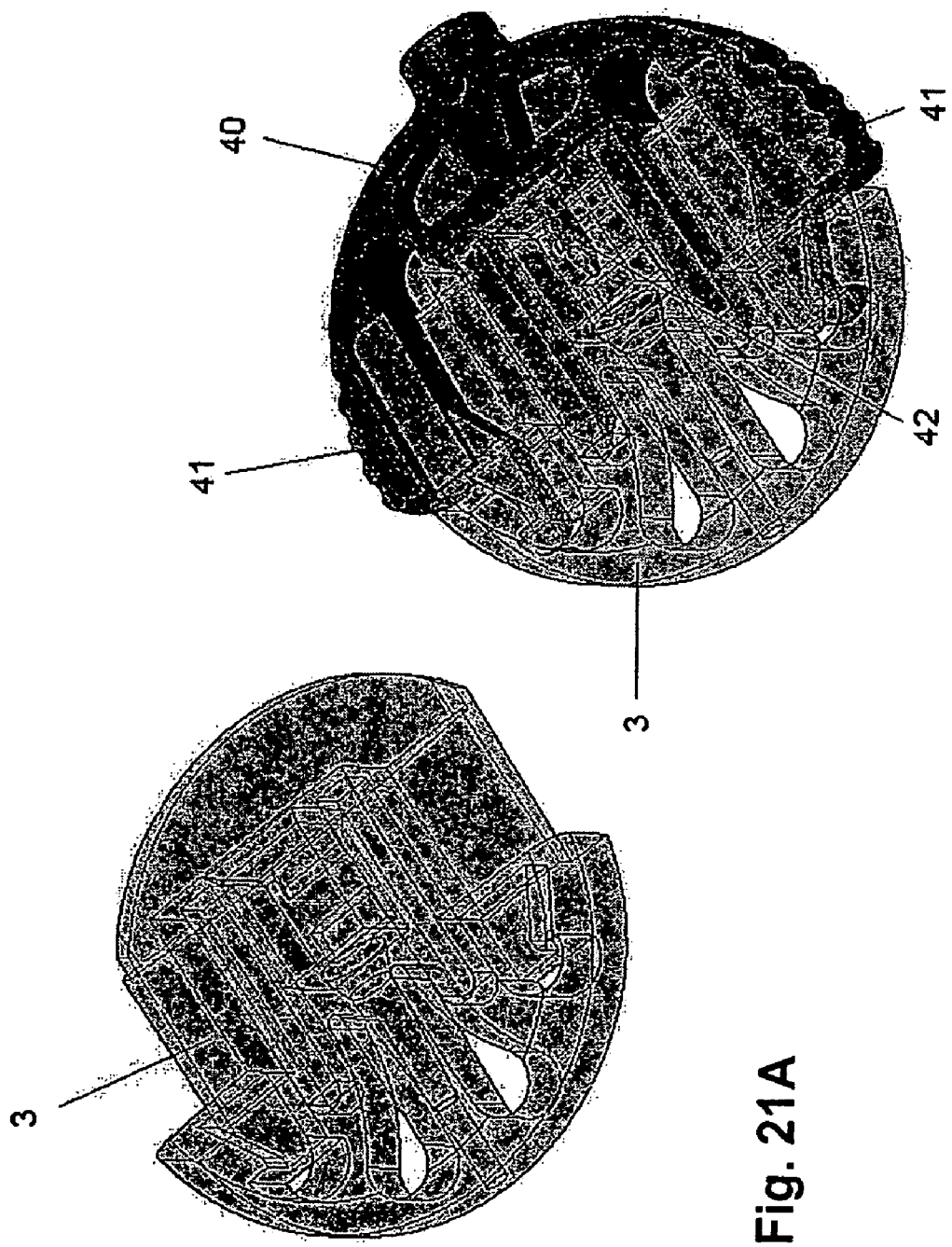

INSERTER

This application claims the benefit of U.S. Provisional Application No. 60/634,940, filed Dec. 10, 2004; U.S. Provisional Application No. 60/679,453, filed May 9, 2005 and U.S. Provisional Application No. 60/699,472, filed Jul. 15, 2005.

TECHNICAL FIELD

The invention relates to an inserter for an infusion set for intermittent or continuous administration of a therapeutical substance, such as e.g. insulin. The inserter comprises a needle unit comprising an insertion needle and a cannula housing comprising a soft plastic cannula to be placed subcutaneously in a patient.

BACKGROUND OF THE INVENTION

EP 688232 B1 relates to a low-profile, angled infusion set comprising a cannula housing with a soft plastic cannula to be placed inside the body of a patient. During insertion the cannula housing is locked to a needle hub and the insertion set is placed by hand i.e. the set does not comprise an inserter.

U.S. 2002/0077599 A1 concerns an inserter for a low-profile, angled infusion set which inserter comprises an inserter housing having a bottom wall, a retainer slidably connected to the inserter housing for movement between retracted and extended positions in a direction substantially parallel with the bottom wall. The inserter also comprises a base member connected to the outer surface of the inserter housing. The retainer is adapted to releasably receive a cannula housing. When used the retainer 30 moves forward and causes the needle 27 and the cannula 26 to pierce the skin at a proper angle and enter into the subcutaneous layer at a proper distance. The cannula housing 28 can then be released from the inserter assembly 10 by depressing the release button 66. Afterwards the mounting pad 80 is secured to the skin and the needle 27 is removed, thus leaving the cannula 26 in place.

This reference concerns a rather complex structure and the complexity necessitates the use of two housing portions, an upper and a lower which portions may be constructed of any suitable material, and can be retained together through screws (23, FIG. 5), interlocking tabs, adhesive, heat-staking or a combination thereof, or any other well-known fastening means.

The inserter described in U.S. Pat. No. 6,293,925 B1 comprises an injector and an insertion set. The injector is designed to place a needle through the skin at a selected insertion angle and with a controlled force and speed of insertion. The injector comprises a spring-loaded plunger having a head for receiving and supporting the insertion set in a position with an insertion projecting outwardly for transcutaneous placement through the skin of a patient. The plunger is designed for retraction and retention to a locked position with a drive spring compressed in a manner applying a predetermined spring force to the plunger head. FIGS. 30 and 31 illustrate how the subcutaneous insertion set 14 is assembled with the injector when preparing the injector for use.

DESCRIPTION OF INVENTION

The object of the invention is to provide a simple, non-expensive inserter for an infusion set which inserter would be easy and safe for the user to handle during use and to dispose of after use.

The invention concerns a disposable, low-profile inserter for an angled infusion set which inserter comprises a set housing, a cannula housing, a needle hub, a spring unit and a carrier body, where the set housing is provided with guiding means on the internal surface for securing the movement of the carrier body, the cannula housing comprises a soft cannula to be placed subcutaneously, the needle hub comprises a needle for piercing of the skin, the cannula housing and the needle hub are releasably fastened to each other and when fastened to each other the needle is adjoined the cannula; preferably the needle is placed inside the cannula;

the carrier body is provided with guiding means on the external surface which secures the movement relative to the set housing (1) from a retracted to an advanced position, the carrier body is connected to release means, and when the release means are manipulated, the carrier body, the cannula housing and the needle hub are forced by the spring unit to an advanced position where the needle and cannula will be placed subcutaneous when the user holds the device against the skin, the needle hub and the carrier body are provided with unreleasable interacting locking means.

"Adjoined" means that the needle is placed adequately close to the cannula to assure the subcutaneously insertion of the cannula whether the needle is placed inside, beside or around the cannula.

According to one embodiment of the invention the needle hub and the carrier body are created as a single unit e.g. by molding together a movable part of the set housing and a needle hub or e.g. by fastening an insertion needle directly to a movable part of the set housing. According to the present invention it is also possible to use an infusion set known per se as for example the set known from EP 688232 B1 forming an unreleasable connection between a carrier body and the needle hub where after the needle unit comprising the carrier body and the needle hub are fastened in the set housing during production of the inserter. The unreleasable connection could be formed e.g. by gluing, welding or by mechanically locking the two units to each other.

In a preferred embodiment the unreleasable connection between the carrier body and the needle hub is formed by making openings in a part of the needle hub which is covered by a solid part of the set housing, and by making corresponding projections in the carrier body. When the set housing is placed around the needle unit ("around" meaning that material of the set housing covers the needle unit on at least two opposite sides) either the elasticity of the set housing will squeeze the two opposite sides together and thereby squeeze the needle hub and the carrier body together, or the confined space created by two opposite sides of an essentially rigid set housing will force the projections of the carrier body and the openings of the needle hub together and form an unreleasable connection between the carrier body and the needle hub as the openings of the needle hub and the projections of the carrier body fit perfectly together.

According to another embodiment of the invention the needle unit is locked to the inserter after use. When the needle unit is locked to the inserter after use it will be possible for the user to remove both the inserter and the needle unit by only grabbing the inserter, instead of the user holding on to both inserter and needle unit after use. According to the embodiment shown in FIGS. 1-3 the needle unit is locked to the inserter because the needle unit can only move in a confined space. The confined space is limited by the U-shaped set housing on three sides, by the guiding means of the set housing and the needle unit on two sides as the guiding means prevents sideways movements and by the stopper 12 which prevents the needle unit from moving forward beyond a fixed point.

According to another embodiment of the invention it is possible to move the needle unit back from the advanced position where the needle can pierce the skin of a patient to a retracted position in order to diminish the risks of getting into contact with the used needle.

According to another embodiment of the invention the lower part of the set housing—where the lower part of the set housing is the side closest to the user during insertion—could be prolonged and turned upward in relation to the base line (the base line is a line parallel to the needle but at a lower level where a "lower level" means a level closer to the user, normally the level provided by the lower side of the set housing). This prolongation or projection of the lower part provides an appropriate contact between the skin of the patient and the inserter in order to have the cannula inserted in a proper angle, and also the prolonged or projecting part lifts up the mounting pad to a proper position for contact with the skin.

The end of the projecting part should preferably pass beyond the line formed by the needle/cannula in front of the end of the insertion needle when the needle unit is in a retracted position. This makes it necessary to provide an opening in the prolongation in order for the needle/cannula to be able to pass through. According to the embodiment of FIGS. 1-3 this is obtained by separating the projecting part into two legs. In this embodiment the projecting part is formed as a mathematical continuous curvature but it could also be non-continuous, i.e. being provided with one or more breaks.

In another aspect of the invention the set housing is made out of a single piece of material. That the needle hub housing is constructed of one piece of material means that no screws or the like is needed to assemble or fasten the casing surrounding the carrier body and the inserter set. The set housing could be produced by molding, i.e. injection molding or by any other known technology. Also the set housing could be produced as e.g. two halves which afterwards are glued or welded together. The set housing could be made of plastic or metal or any other suitable material having the necessary mechanical properties.

The inserter according to the invention is of a simple construction and consists of relatively few parts and thus it will be less expensive to produce and assemble. This renders the inserter especially suitable for use as a disposable product.

In yet another embodiment the set housing is formed of a single U-shaped piece of material. The set housing is U-shaped which means that it is constructed of a rectangular or elliptic piece of flat material which is bent in such a way that the ends of the material—seen from the side—forms two substantial parallel legs connected in one end with a straight or arched line, where the legs are not necessarily of the same length. The material is of a bent form which does not mean that it is constructed by bending; it could e.g. be molded in a bent form. When the set housing is U-shaped the part called the lower leg is the leg in contact with the user when the inserter is in position for insertion of the infusion device.

In another embodiment the set housing is formed as a piece of pipe with a rounded or poly-sided cut-through profile.

In yet another embodiment the spring unit is fastened to the set housing in a first position and to the carrier body or the needle unit in a second position, where the first position is situated closer to the front end of the set housing than the second position when the spring unit is biased, where the front end of the set housing is the end of the set housing nearest the user during insertion. This feature will result in that the carrier body and the needle hub which are forming a single unit is pulled forward relative to the housing when the release means are activated. The spring unit could be made of any material which retracts to a relaxed unbiased position, preferably made of rubber, plastic or metal.

DESCRIPTION OF THE DRAWINGS

The invention is explained in greater detail below with reference to the accompanying drawings wherein a preferred embodiment of the invention is shown.

FIGS. 15A and 15B show a seventh embodiment with a coiled spring unit seen from the side in (A) a forward position and (B) a retracted position;

FIGS. 17A-D show a ninth embodiment with a spring unit fastened to opposite sides of the set housing and the embodiment is shown in (A) a forward position seen from the side, (B) a retracted position seen from the side, (C) a forward position seen from above, (D) a retracted position seen from above;

FIG. 21A shows a cannula housing of an infusion set which can be inserted with the inserter of the invention;

FIG. 21B shows a cannula housing and a connector of an infusion set which can be inserted with the inserter of the invention.

Figure 1:
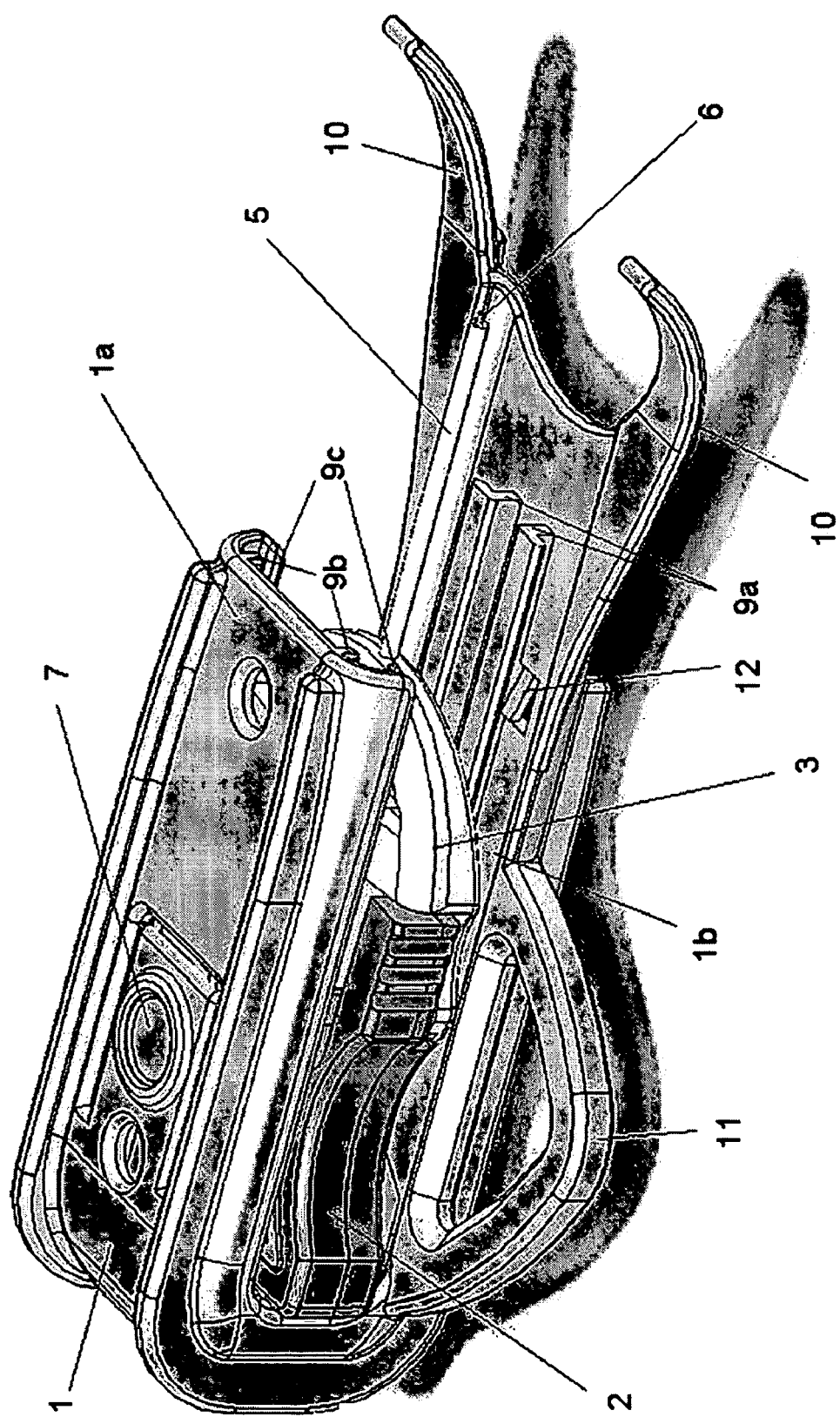
FIG. 1 is an upper/side view of an embodiment of the inserter of the invention with the infusion set in a retracted position.
Figure 2:
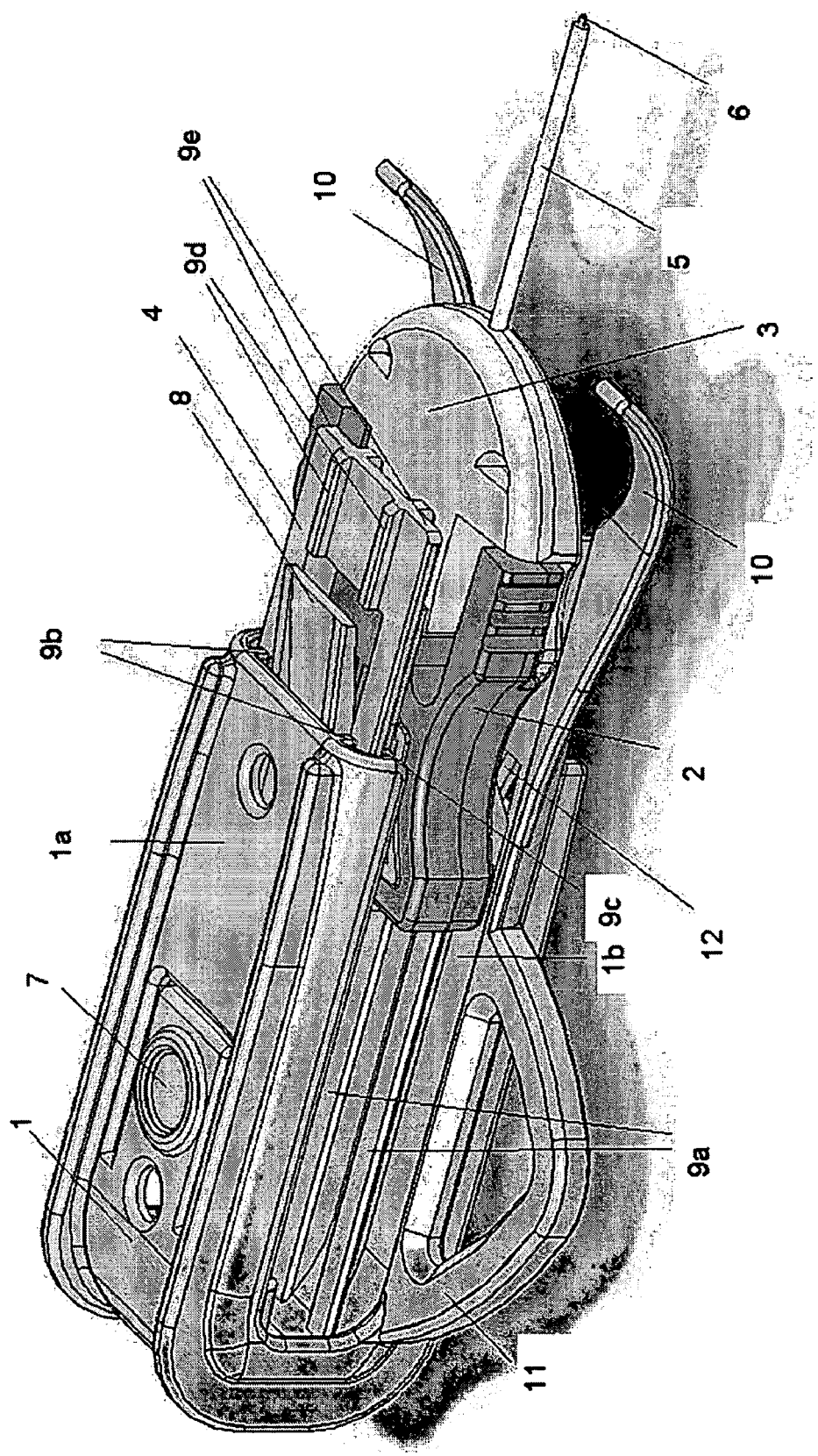
FIG. 2 is an upper/side view of the inserter with the infusion set in an advanced position.
Figure 3:
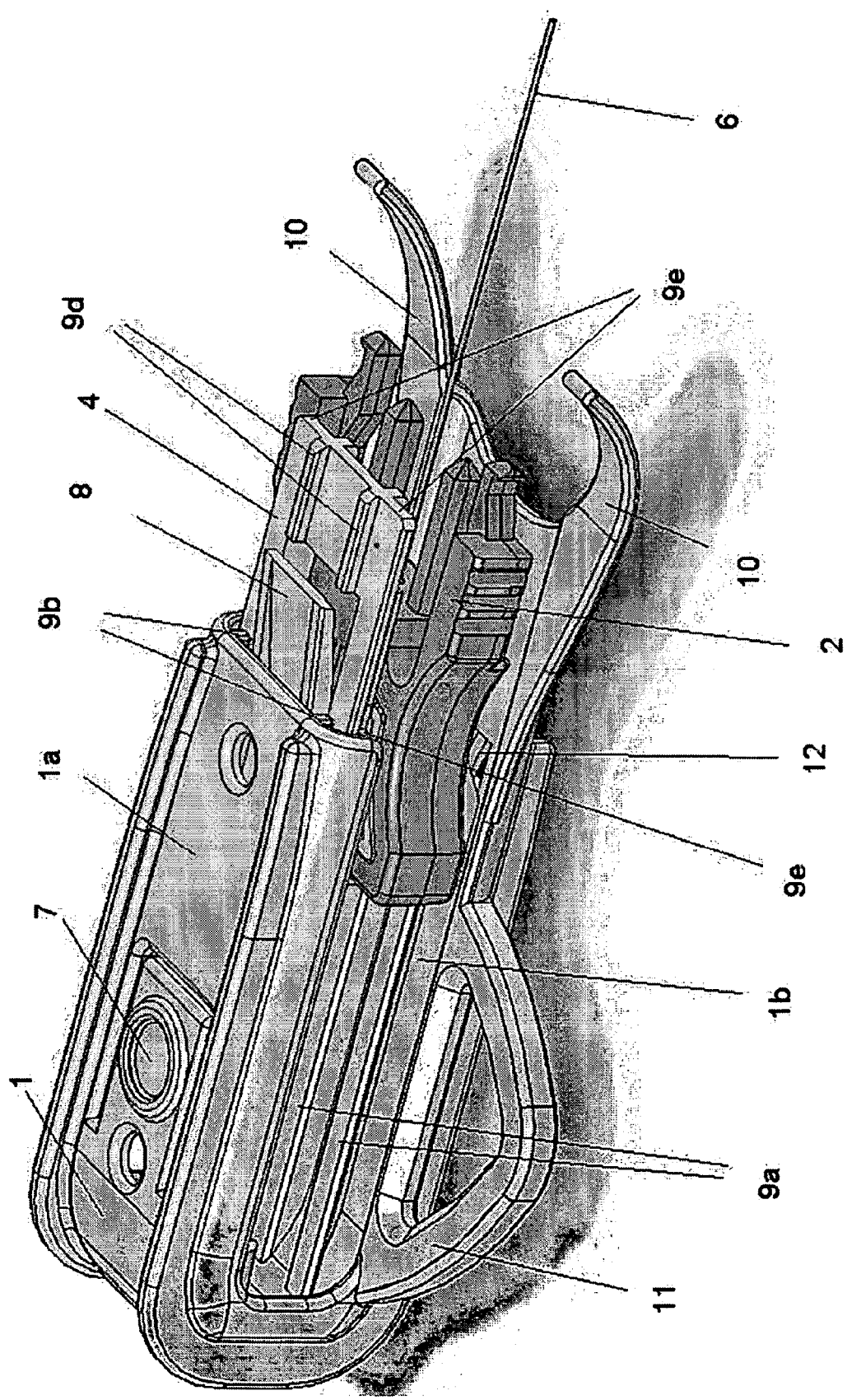
FIG. 3 is an upper/side view of the inserter with the infusion set in an advanced position where the cannula housing has been detached from the needle unit.

The inserter set of FIGS. 1-3 comprises a set housing 1, a needle unit which in this embodiment is constructed of a needle hub 2 comprising an insertion needle 6 and a carrier body 4 unreleasably connected to the needle hub 2, and a cannula housing 3 comprising a laterally projecting cannula 5.

Figure 4:
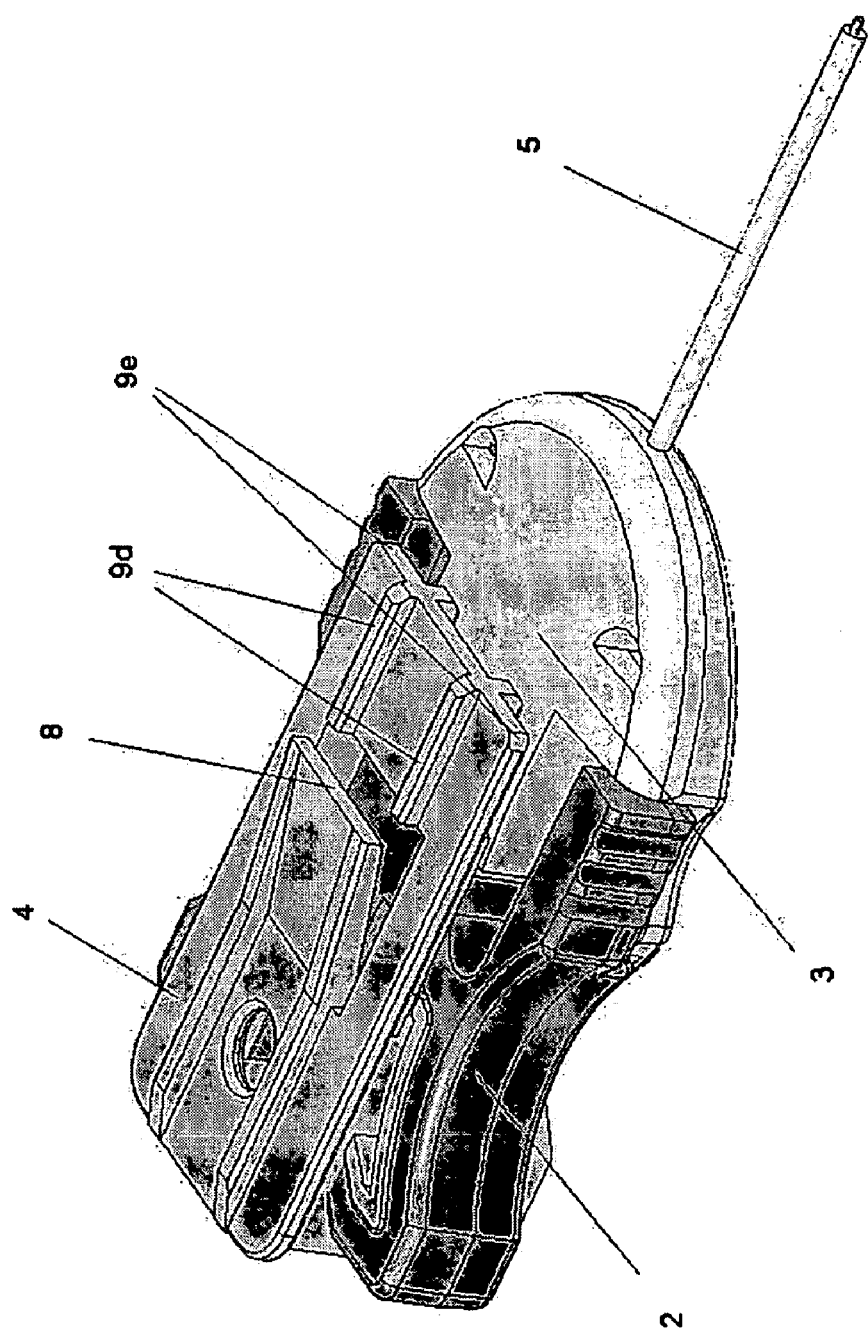
FIG. 4 is an upper/side view of the needle unit attached to the cannula housing.

The set housing 1 is provided with a release button 7 which button when activated will release the spring unit 13 and cause the needle unit 2, 4 and the cannula housing 3 to move forward to an advanced position. When the release button 7 is activated, a flexible part 8 of the needle unit is pushed down and released from a not shown stop. The flexible part 8 is shown on FIGS. 2, 3 and 7 where the needle unit is in an advanced position and on FIG. 4 where the needle unit is shown isolated from the set housing 1.

FIGS. 1-3 and 5-7 show an embodiment of the invention wherein the set housing 1 is U-shaped having an upper leg 1a and a lower leg 1b. In this embodiment the upper and the lower leg are parallel and connected in one end through a piece of material approximately of the same length as the height of the needle unit 2, 4. The distance between the upper and the lower leg 1a, 1b will depend on height and general shape of the needle unit 2, 4 connected with the cannula housing 3 and also the distance between the upper and lower leg 1a, 1b should be sufficient to comprise the guiding means 9a, 9b, 9c which keep the needle unit 2, 4 and cannula housing 3 in place during traveling between the retracted and advanced position.

The guiding means of the set housing in FIGS. 1-3 comprises two opposite and outward L-profiles 9a standing up from the lower leg 1b, flanges 9b extending downwardly from the upper leg 1a and flanges 9b extending inwardly from side parts of the upper leg 1a being in contact with the sides 9e of the needle unit 2, 4. The corresponding guiding means on the needle unit 2, 4 comprise at the bottom side of the needle unit 2, 4 two inward L-profiles (not shown in figures) which profiles correspond to the outward L-profiles on the set housing 1, see FIG. 5, and on the upper side of the needle unit 2, 4 two flanges 9d are standing up from the top side keeping contact with the upper leg 1a and the flanges 9b.

At the end of the lower leg 1b two upwardly bent parts 10 are formed. These parts 10 indicate the correct insertion angle for the user when the user inserts the cannula. Also the parts 10 will assure that a mounting pad 14 placed in connection with the cannula housing 3 will be in correct and ready position when the cannula 5 is inserted.

The essentially triangular profile 11 extending from the lower leg 1b is provided for facilitating handling as the total functional inserter set is quite small and else can be difficult to handle if the user has reduced dexterity.

Figure 6:
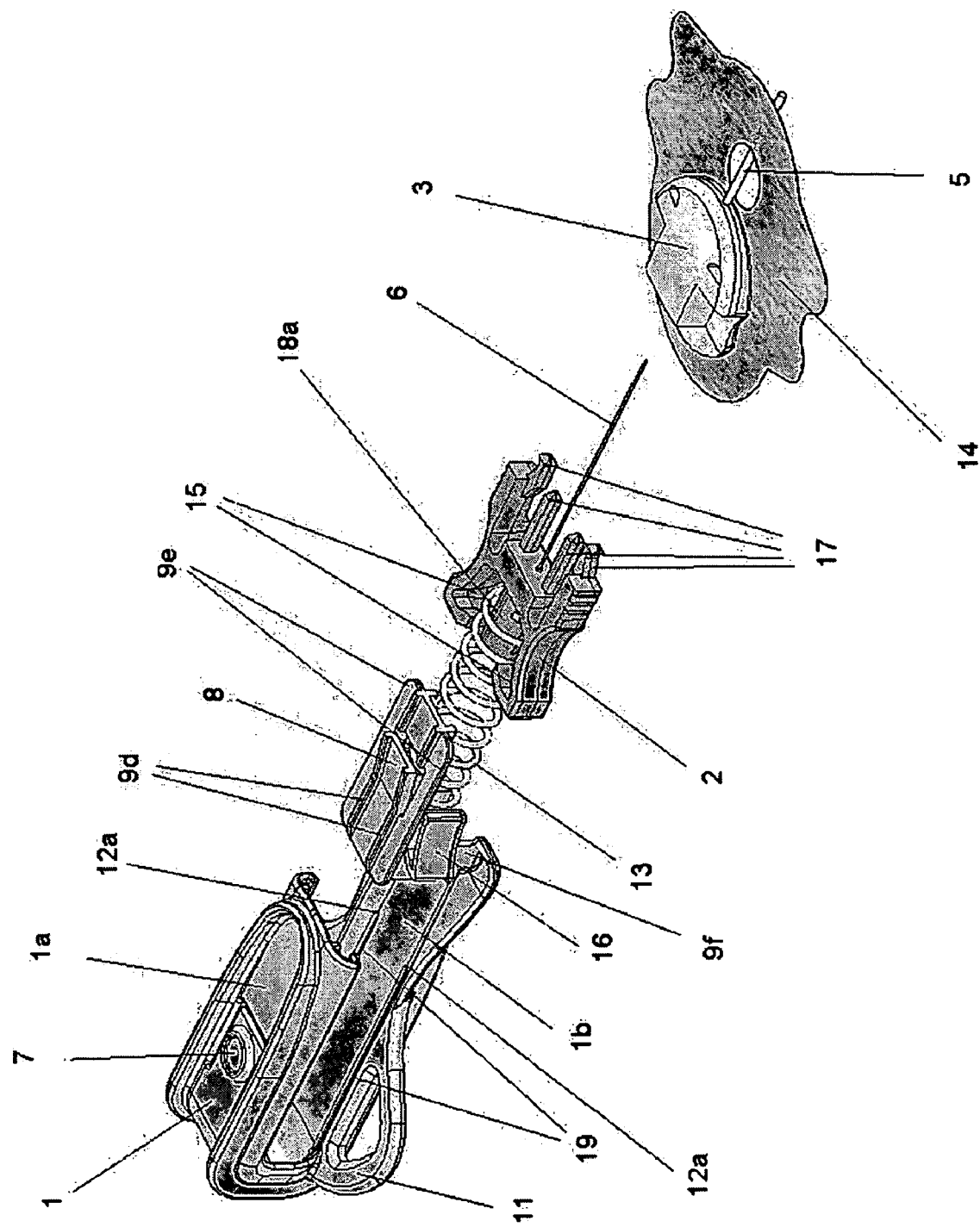
FIG. 6 is an upper/side exploded view of the inserter shown in FIG. 5 with the infusion set.
Figure 7:
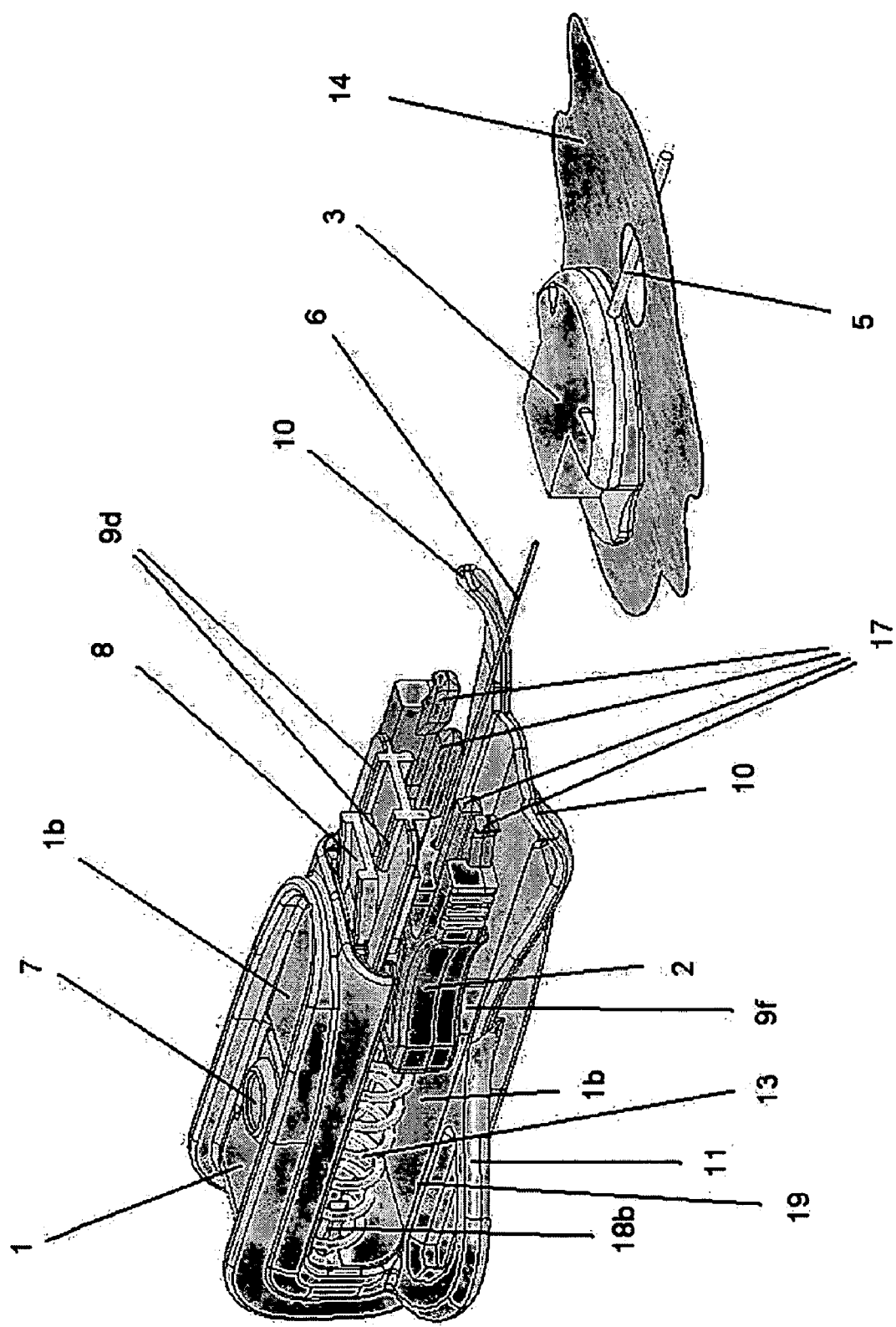
FIG. 7 is an upper/side view of the inserter shown in FIG. 5 where the needle unit is detached from the cannula housing and in an advanced position.

The spring unit 13 that pushes the needle unit 2, 4 forward when the release button 7 is activated, is shown in FIGS. 6 and 7. The spring unit 13 is placed between the set housing 1 and the needle unit 2, 4 at the closed end of the U-shaped set housing 1. The spring unit 13 is fastened to a protrusion 18a at the back end of the needle hub 2 and to a protrusion 18b on the inside of the set housing 1. The spring unit 13 may be any suitable spring but in this embodiment the spring unit 13 is preferably a coil spring which pushes the needle unit 2, 4 away from the set house ending.

The spring unit 13 could also be a flat spring placed between the set housing 1 and the needle unit 2, 4 at the closed end of the U-shaped set housing 1, or the spring unit 13 could form an elastic connection between the front of the set housing 1 and the back of the needle unit 2, 4 pulling the needle unit 2, 4 forward.

In order to control the forward movement of the needle unit 2, 4 when the release button 7 is used, the lower leg 1b of the set housing 1 is provided with a stopper 12. In the embodiment in FIGS. 1-3 the needle unit 2, 4 stops moving forward when a corresponding protrusion on the needle unit 2, 4 hits the stopper 12. In the embodiment in FIGS. 5-7 two flanges 9f move in tracks 19 formed as grooves in the lower leg 1b and the stopper 12a is provided as the flanges 9f touches the end of one or both of the tracks 19.

If there is no stopper 12 to stop the needle unit 2, 4 from moving forward, the needle unit 2, 4 will stop when the front of the needle unit touches the skin of the user. The use of a stopper 12 will make it easier to control the dept of insertion, and also the stopper 12 can lock the needle unit 2, 4 to the set housing 1 making it possible to remove inserter and needle unit 2, 4 as a single item after use.

In another preferred embodiment the stopper 12 is created by the ends of the upper and lower legs 1a and 1b of a U-shaped set housing 1. When both or one of the ends of the legs 1a and 1 b are turned inwardly, the leg ends restrict the distance between the upper and the lower leg 1a, 1b at the open end of the U-shaped set housing. When this distance is restricted to less than the height of the needle unit 2, 4, the inwardly turned leg ends perform as a stopper 12.

Figure 5:
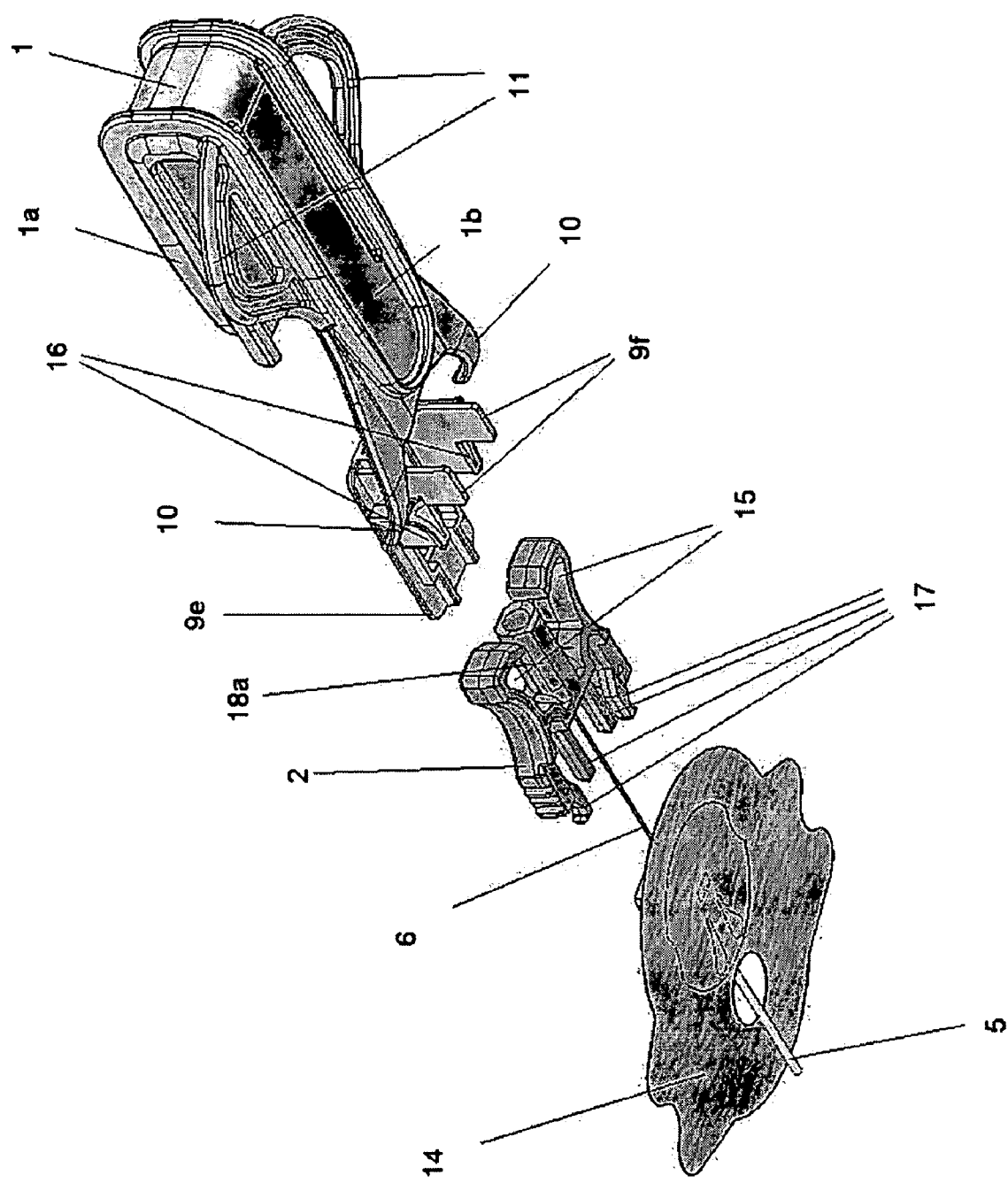
FIG. 5 is a lower/side exploded view of another embodiment of the inserter with the infusion set.

In FIG. 5 the needle hub 2 is shown detached from the cannula housing 3 and the carrier body 4. In this preferred embodiment the needle hub 2 comprises two openings 15 in the rear half which openings 15 correspond to two projections 16 on the carrier body 4. When the projections 16 are placed in the openings 15, the needle hub 2 and the carrier body 4 are locked relatively to each other in the horizontal plane (in this embodiment the horizontal plane is the plane perpendicular to the contact surfaces between the openings of the needle hub 2 and the projections of the carrier body 4). When the needle unit 2, 4 comprising the joined needle hub 2 and carrier body 4 is placed in the set housing 1, the legs 1a and 1b of the set housing 1 cover the needle unit 2, 4 on two opposite sides and prevent movements in the vertical direction.

When the inserter set is produced and prepared for use, it will normally be delivered to the user in packed, set and sterilized condition being ready for use. When the user opens the package, the needle unit 2, 4 is connected to the cannula housing 3 forming the infusion set, and the infusion set is in a retracted position. A mounting pad 14 is placed on the lower side of the cannula housing 3 and the sticky side of the mounting pad is covered with release paper. The user removes the release paper from the mounting pad and places the base part 1b, 10 of the inserter against the skin in an adequate angle; where after the user pushes the release button 7.

When pushing the release button 7 the needle unit 2, 4 together with the cannula housing 3 are released and pushed forward to the advanced position, and the cannula will be placed subcutaneously as the insertion needle 6 placed inside the cannula 5 pierces the skin.

The cannula could be of a known type as for example described in EP patent no. 688232 where the cannula 5 is arranged in a rectilinear bore through the cannula housing 3. The cannula housing according to this document comprises two guide openings and two locking openings in addition to the through bore. These openings are symmetrically shaped about a plane including the central axis of the through passageway and extending perpendicular to the rear side. The guide openings are elongated openings of a substantially square cross section which openings are adapted to receive mating guide pins 17 on a connecting needle or connecting hub. In FIGS. 3, 5, 6 and 7 where the needle unit 2, 4 is separated from the cannula housing 3 it is possible to see the guide pins 17 of the needle hub 2.

When the cannula 5 and the cannula housing 3 covered with the mounting pad 14 is in place, the user unlocks the cannula housing 3 from the needle unit 2, 4 and removes the remains of the inserter set which comprises the set housing 1 and the needle unit which is locked to the set housing 1. In EP patent no. 688232 an appropriate releasable connection between a cannula housing and a needle hub is illustrated and the example is hereby incorporated by reference.

In order to dispose of the used inserter remains in a secure way, the user can pull the needle unit 2, 4 back into a retracted position and replace the inserter remains in the opened package.

After having disposed of the inserter and the needle unit the user can connect the cannula housing 3 which is now fastened to the user's skin, to a connecting hub.

The connecting hub can be connected to a luer coupling member through a hose. Through the luer coupling it is possible to administer a suitable therapeutical substance, such as insulin from a pump. The connecting hub can also be a closing part with a suitable entrance for the inserting needle of a syringe. Such a closing part can stay in position for up till three days while the user can have medication, e.g. insulin injected through the entrance in order to reduce trauma to the skin.

Figure 8:
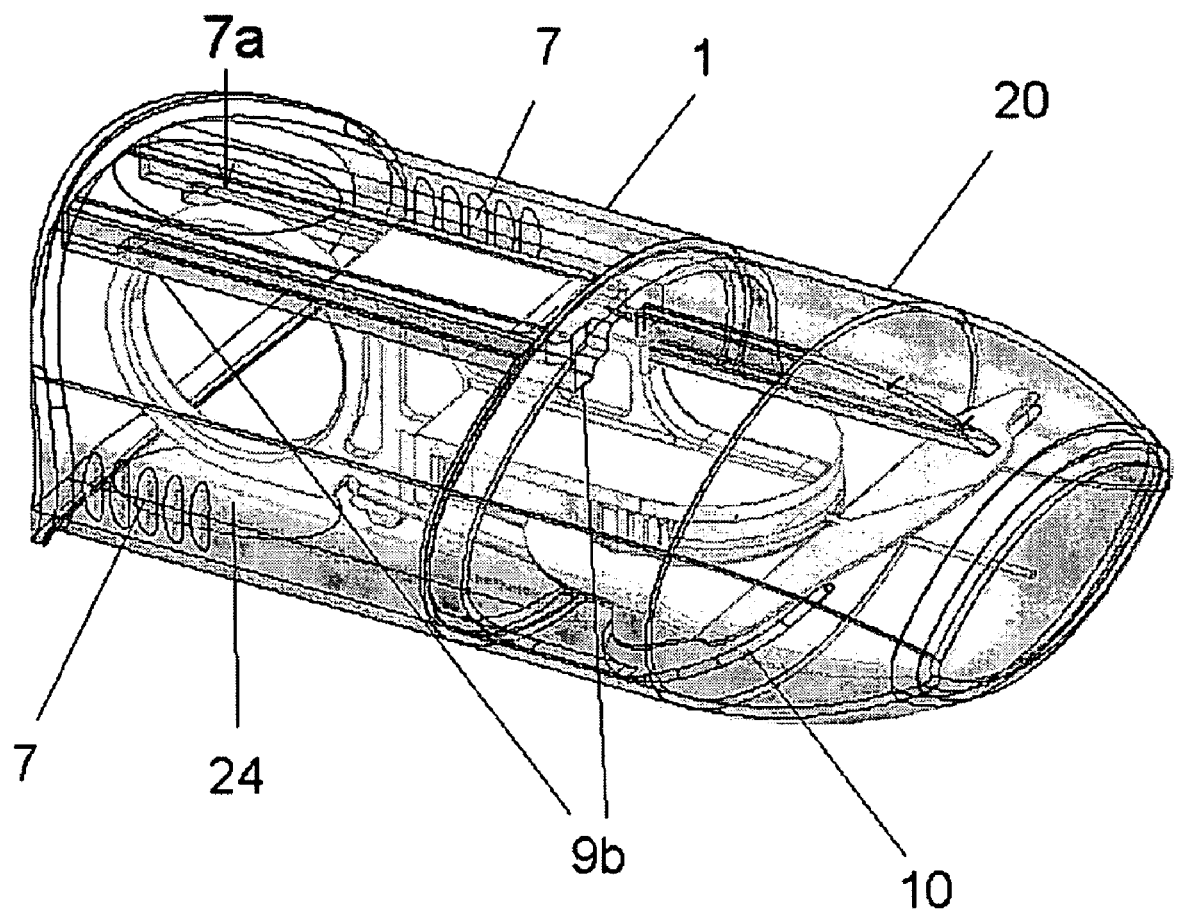
FIG. 8 is an upper/side view of a third embodiment of an inserter placed ready for delivery.
Figure 9A:
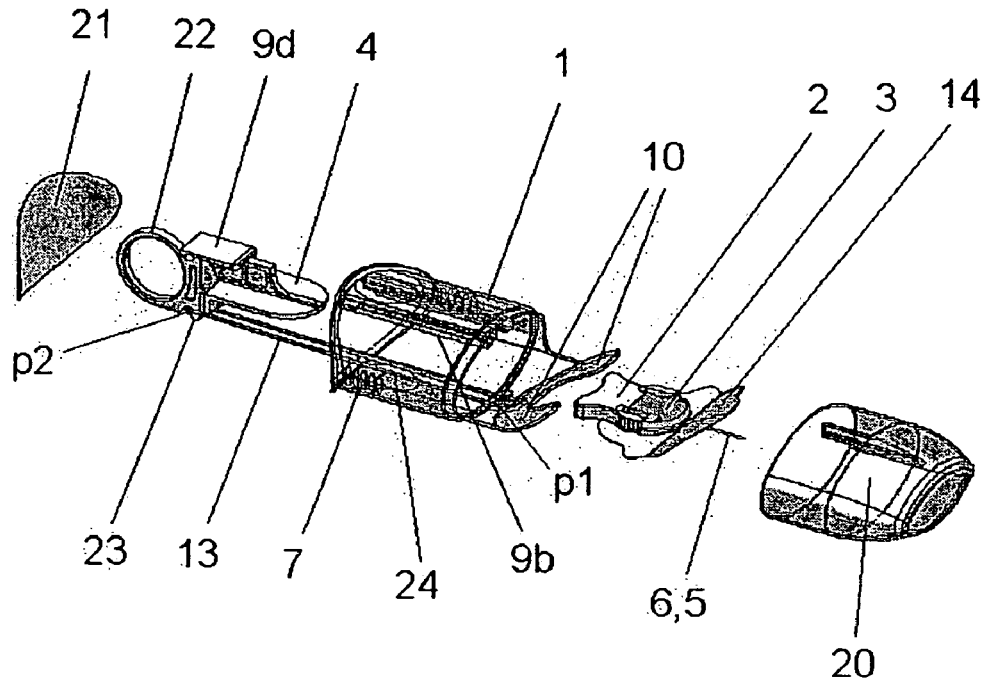
FIG. 9A and 9B show an exploded view of the third embodiment.
Figure 9B:
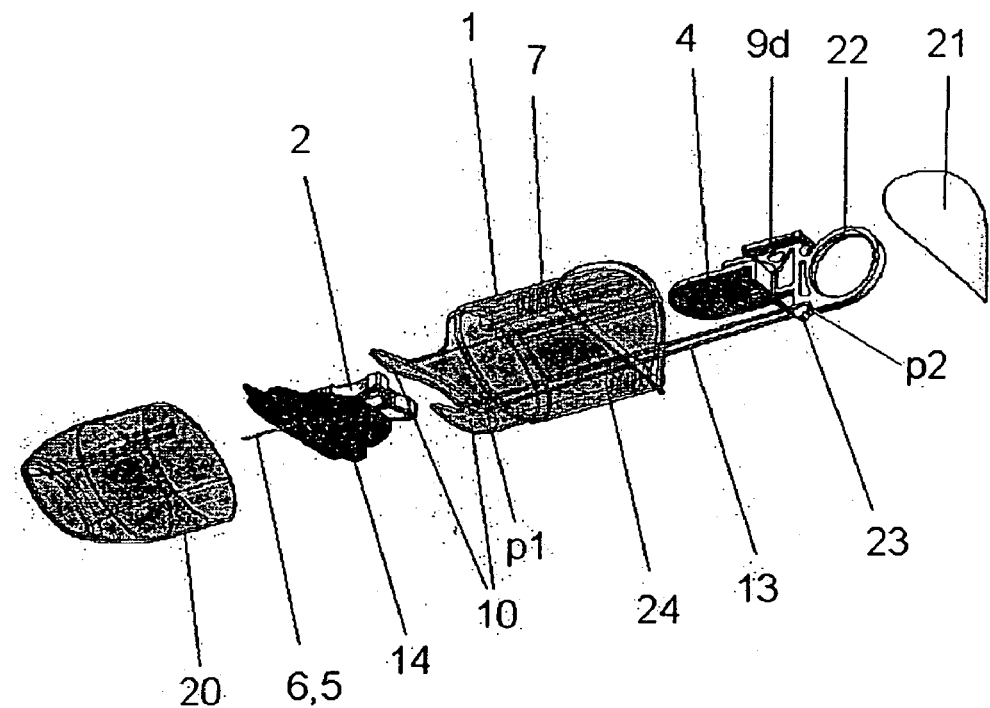
Figure 10:
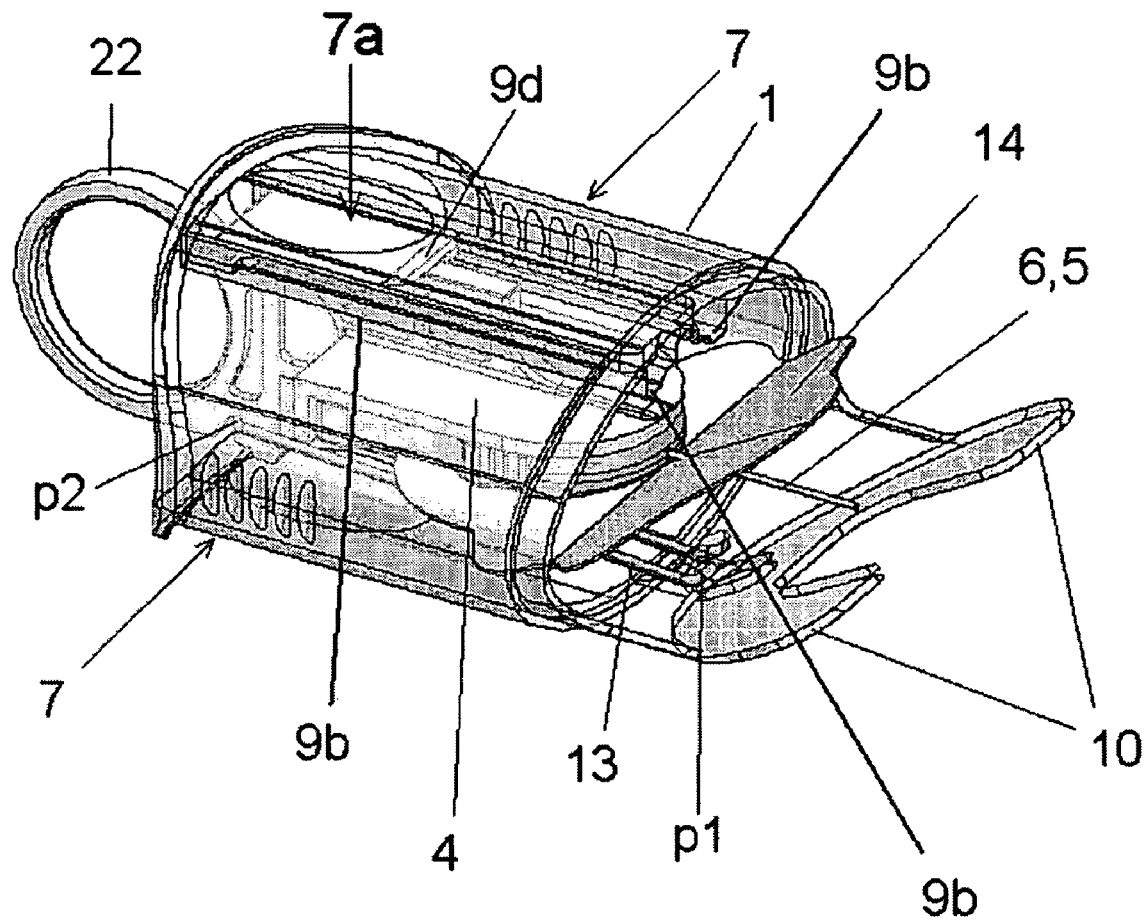
FIG. 10 shows the carrier body of the third embodiment in a retracted position ready for insertion.

The inserter set according to a third embodiment shown in FIGS. 8-10 comprises a set housing 1, a needle unit constructed of a needle hub 2 comprising an insertion needle 6 and a carrier body 4 unreleasably connected to the needle hub 2, and a cannula housing 3 comprising a cannula 5.

In FIG. 8 it is shown how this embodiment could be delivered: the needle unit 2, 4 is in a relaxed, i.e. non-biased or just slightly biased forward position and the needle is covered with a hard case top 20 which has to be removed from the device before use. The set housing 1 is formed as a piece of pipe with an oval cut-through profile. Opposite the hard case top 20 the set housing 1 is covered with a removable flat cover 21. The flat cover can be provided with an adhesive for assuring the tight closure between the cover 21 and the set housing 1 or it can be welded to the set housing, and any kind of cover which at the same time has the necessary strength to resist transportation and can provide hermetical sealing of the device will do. The needle unit 2, 4 is unreleasably connected to a handle 22 which handle on the lower side is provided with a projection 23 for fastening of a spring unit 13 (see FIGS. 9A and 9B). The upper side of the carrier body 4 is provided with guiding means 9*d* having the form of a rectangular plate, the guiding means 9*d* of the carrier body 4 fit into guiding means 9*b* of the set housing 1 having the form of downward L-profiles.

The combination of the L-profiles and the rectangular plate assures that the carrier body has limited possibilities for moving up and down, and is lead along the wall of the set housing 1 in a very controlled manner. The spring unit 13 in this embodiment consists of elastic in the form of an O-ring. The spring is fastened to the lower front part of the set housing 1 at the position p1 and the lower part of the carrier body 4 at position p2. In this embodiment the spring unit 13 is fastened behind—and beyond—the carrier part of the carrier body 4 which causes the carrier body 4 to get into a slightly tilted position when the spring is biased as only the lower part of the carrier body 4 is pulled forward by the spring unit 13, and this tilted position can lock or support the locking of the carrier body 4 in the retracted position as the guiding means 9*d* are provided with a protruding part 30 (see FIGS. 12A-12C, 15A, 15B, 19 and 20) on the rearmost half. When the spring unit 13 is biased, this protruding part 30 will be influenced by a downward force created because the carrier body 4 is being pulled forward at a low point.

When the user is going to apply the device the needle unit 2, 4 is brought to a retracted position (see FIG. 10) by pulling the handle 22 either (1) until the projection 23 on the lower side of the handle passes a raised part 24 on the inside of the lower part of the set housing 1 or (2) until the protruding part 30 on the guiding means 9*d* passes the end of or an opening in the L-profiled guiding means 9*b* of the set housing 1. Then the user places the upwardly bent parts 10 against the skin and release the needle unit 2, 4.

When the user wants to release the needle unit 2, 4 from the retracted position the user can push the release button 7 (shown in the form of two pressure points) together if the needle unit is locked by (1) or the user can push down at 7*a* if the needle unit is locked by (2). Preferably there will be indicated pressure points 7*a* on both upper and lower side of the set housing 1 in order for the user to apply oppositely directed finger pressures. When the two points of the release button 7 are pushed toward each other the diameter of the housing perpendicular to a line between the pressure points is increased, and as the guiding means 9*d* on the upper side of the carrier body 4 are caught in the inward L-profiles the projection 23 is lifted free of the raised part 24. This activates the spring unit 13 and causes the needle unit 2, 4 and the attached cannula housing 3 to move forward to an advanced position. When pushing down at 7*a* the user pushes down the front end of the guiding means 9*d* and disengage the protruding parts at the rear end of the guiding means 9*d* from the means 9*b* of the set housing 1, this activates the spring unit 13 and causes the needle unit 2, 4 and the attached cannula housing 3 to move forward to an advanced position.

Figure 11:
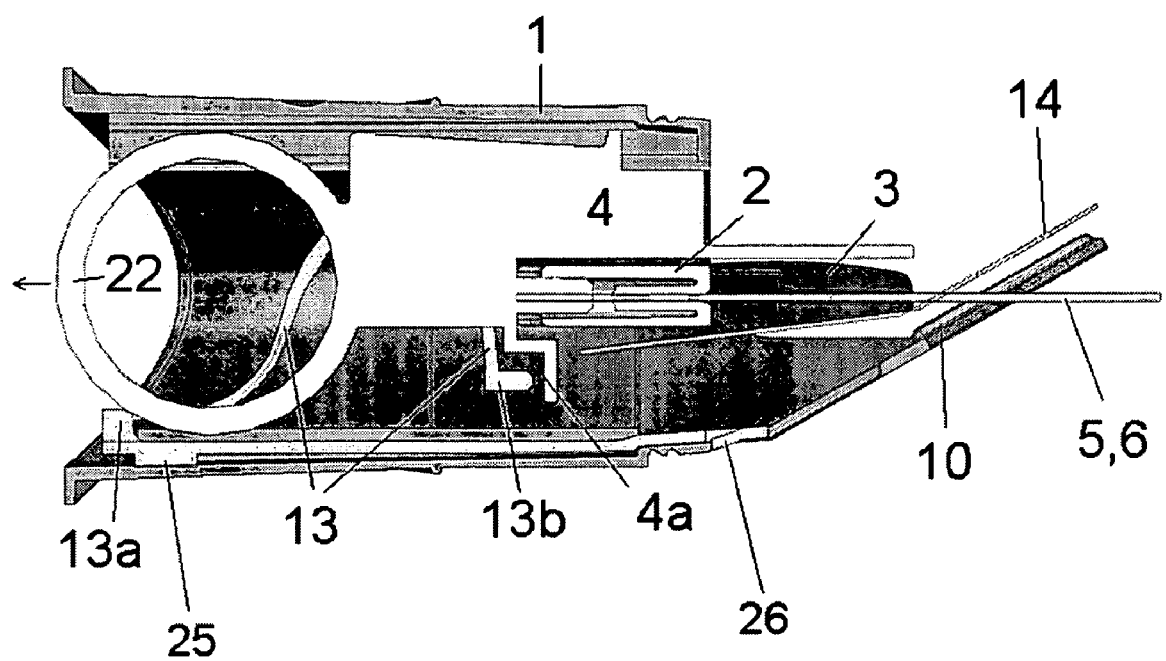
FIG. 11 shows a side view of a fourth embodiment with C-formed spring units.
Figure 12A:
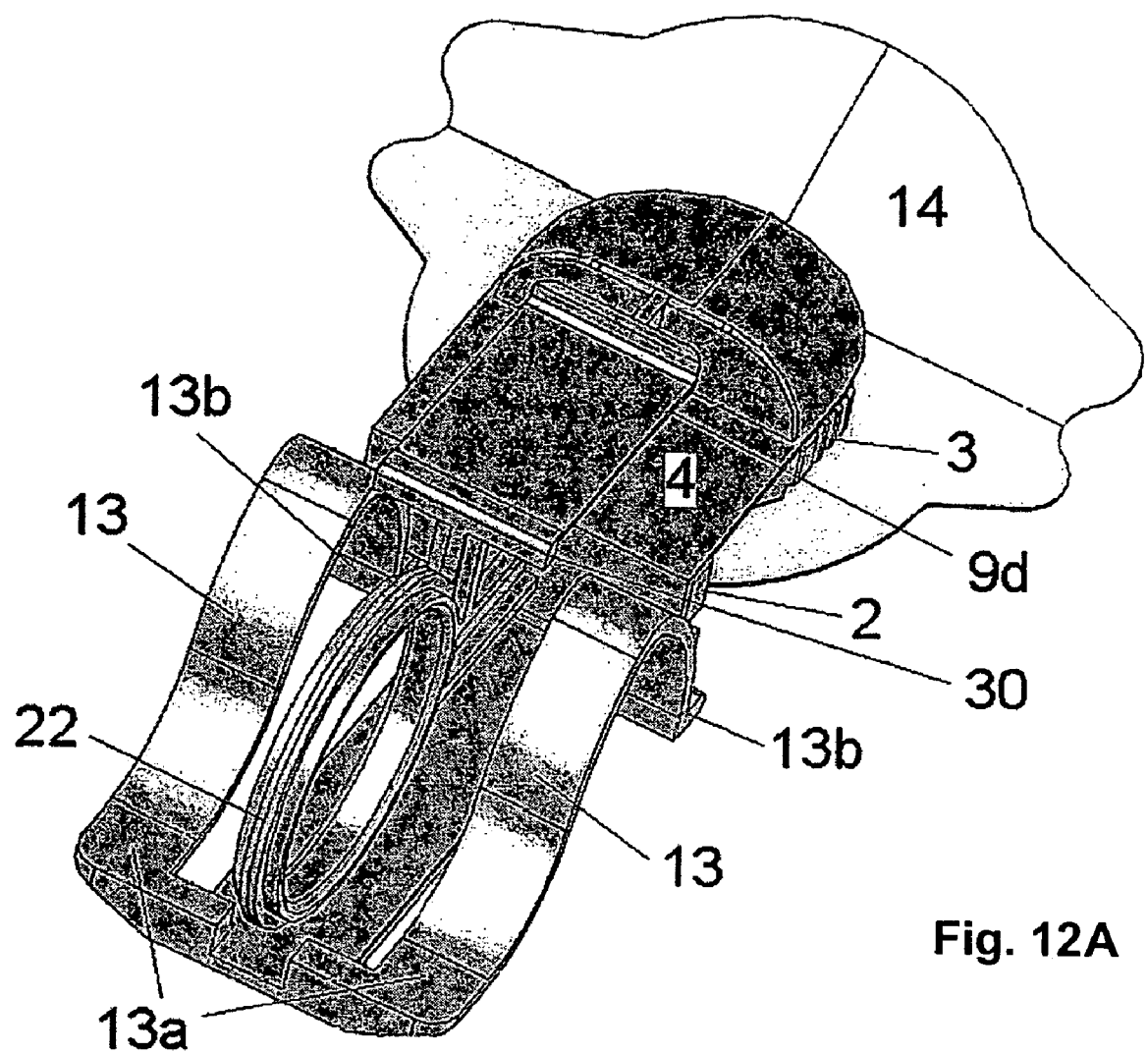
FIG. 12A shows the needle unit combined with the spring unit of the fourth embodiment seen from above/behind.

In FIG. 11 and 12A is shown a fourth embodiment with a different kind of spring unit 13. The spring unit 13 of this embodiment is made of two flat springs and each of them is formed as a C when the spring unit is unbiased. That the flat springs are formed as a C means that they comprise only one convex curve, how the springs are shaped and fastened at each end, 13*a* and 13*b*, of the curve will depend on the material and the form chosen for the springs. The flat springs 13 are fastened to the bottom wall of the set housing 1 in such a way that the back end 13*a* of the C-formed spring units 13 are stationary in relation to the set housing 1. The front end 13*b* of the flat springs rests against a surface 4*a* of the needle unit 2, 4 or is fastened to the needle unit 2, 4. In this embodiment the C-formed spring units 13 are placed between the back end of the needle unit 2, 4 and the back end of the set housing 1 and when the handle 22 is pulled back, the spring units 13 are biased, the two ends of the C-formed spring units, 13*a* and 13*b*, are brought closer together. When the release button 17 is activated the spring units 13 will return to the unbiased form and the needle unit 2, 4 will be pushed forward.

Figure 12C:
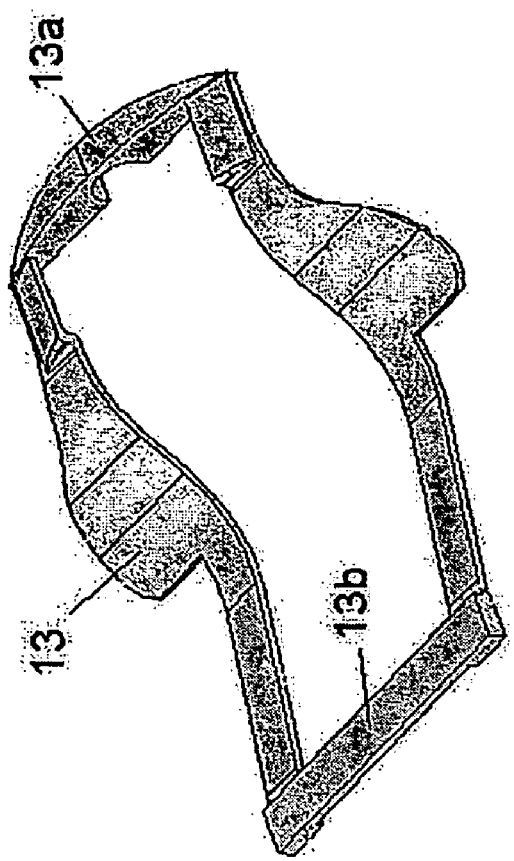
FIG. 12C shows a spring unit similar to the fourth embodiment seen from above/front.
Figure 12B:
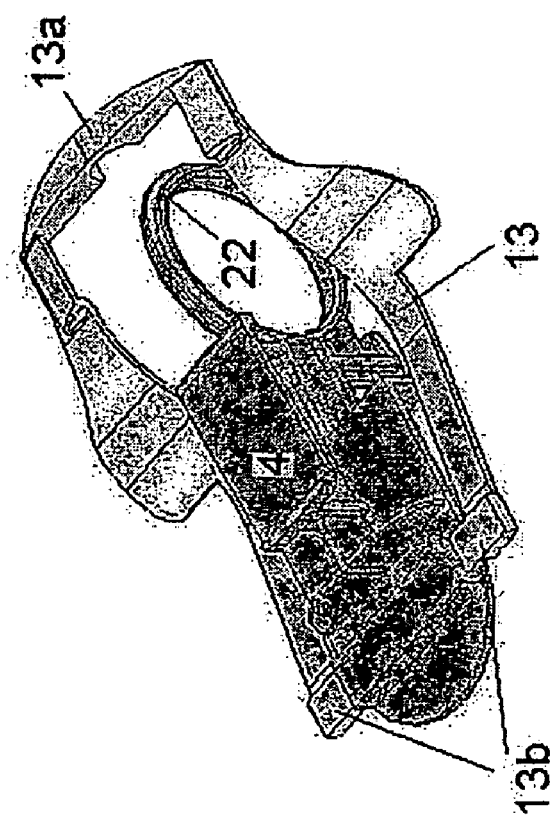
FIG. 12B shows a spring unit and a needle unit similar to the fourth embodiment seen from above/front.

In FIGS. 12B and 12C is shown an embodiment of the flat springs 13 are fastened to the top wall of the set housing 1 in such a way that the back end 13a of the slightly C-formed spring units 13 are stationary in relation to the set housing 1. The front end 13b of the flat springs rests against a surface of the needle unit 2, 4 or is fastened to the needle unit 2, 4 but the front end 13b is in this embodiment fastened to the front part of the needle unit 2, 4 below the needle level.

How the flat springs are fastened to the set housing 1 at 13a will depend on which material they are made of as this influence the form—particularly the thickness—they are made in. If the flat springs are made of a plastic material the material where they are fastened to the housing 1 can take almost any form if they e.g. are produced by molding. If the material is of an adequate thickness a protruding part 25 of the flat spring can be squeezed into an opening in the set housing 1. If the flat springs are made of e.g. metal it would be more expensive to form a protruding part 25 on the flat spring, in this case it would in stead be efficient to cut e.g. a three-sided rectangular slit in the flat spring which is to be fastened to the set housing 1 and form a cut-out 26. This slit makes it possible to bend the cut-out 26 out of the surface of the flat spring and let it rest against the set housing 1. When the flat springs are fastened to the set housing 1 either by a protruding part 25 or by a cut-out 26 it will not be necessary to perform further fastening of the springs to the housing e.g. by welding, gluing or the like.

Figure 13B:
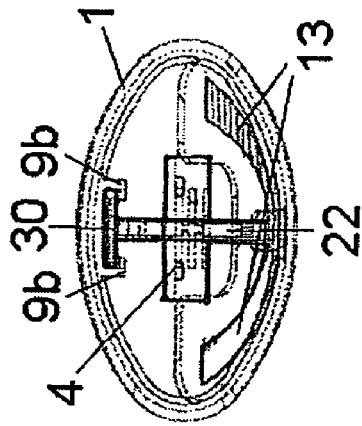
FIGS. 13A-13C show a fifth embodiment with a circular spring seen from the side A, from above B and from behind C.
Figure 13A:
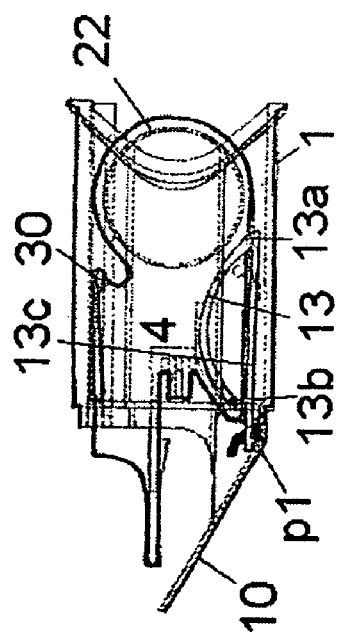
Figure 13C:
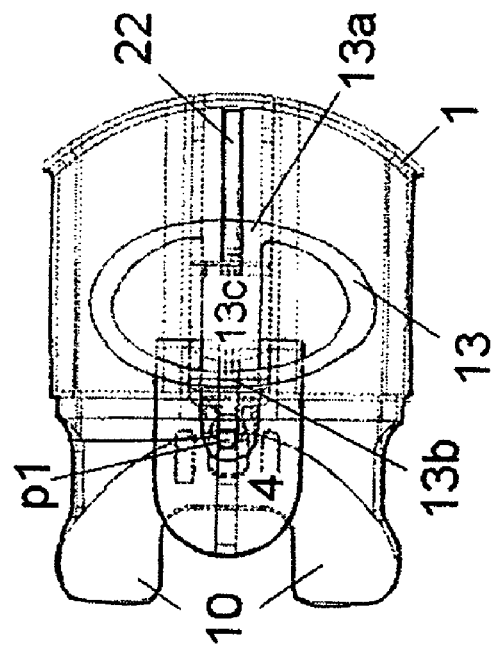

FIGS. 13A-13C show a fifth embodiment of the inserter where the spring unit 13 is formed of a circular spring. The rearmost part 13a of the circular spring unit 13 is stationary to the set housing 1 and the front part 13b of the circular spring 13 is fastened to the needle unit 2, 4 or to the handle 22 or is simply resting against the movable needle unit 2, 4 or handle 22 in a slightly biased state. The spring unit 13 might be formed with a prolonged part 13c lying along the bottom wall of the set housing 1. Such a prolonged part 13c could be fastened anyway along its length but preferably at a position p1 close to the front of the set housing 1.

Figure 13E:
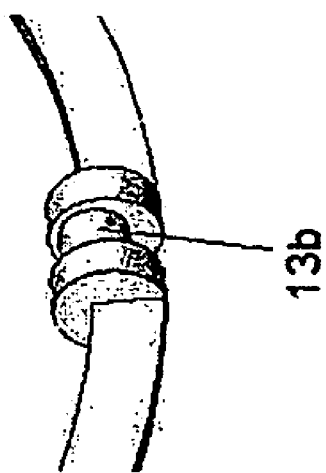
FIG. 13E shows a front view of a portion of the spring shown in FIG. 13D.
Figure 13D:
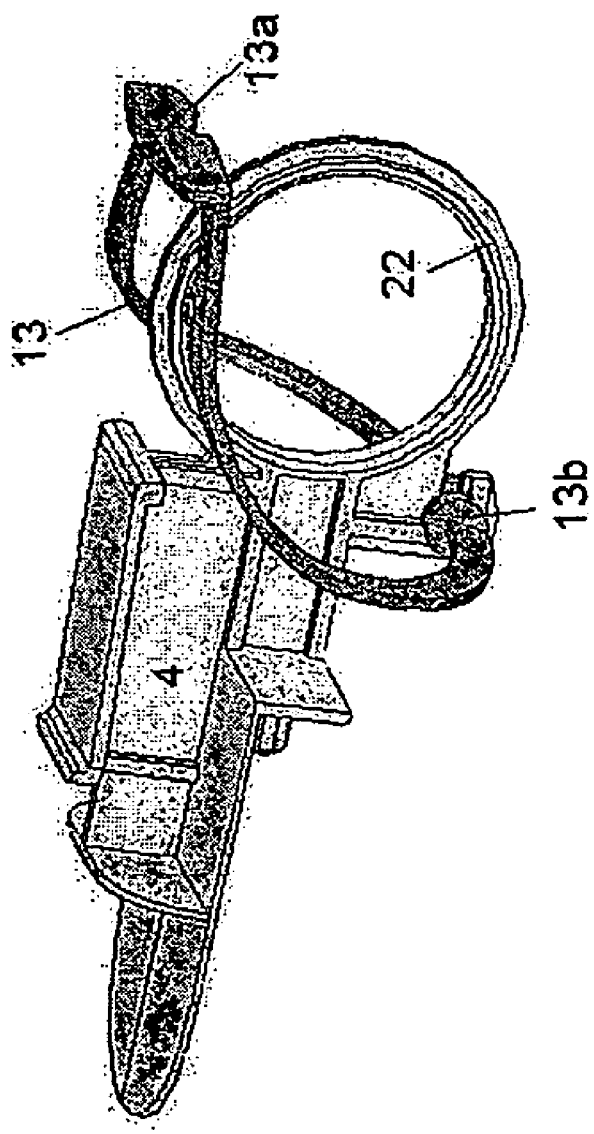
FIG. 13D shows a secondary embodiment with a circular spring seen from the side.

FIGS. 13D and 13E show an embodiment where the rearmost part 13a of the circular spring unit 13 is resting against the upper part (above needle level) of the set housing 1 and the front part 13b of the circular spring 13 is fastened to the handle 22 by simply resting a specially formed part against the handle 22 in a slightly biased state.

Figure 14:
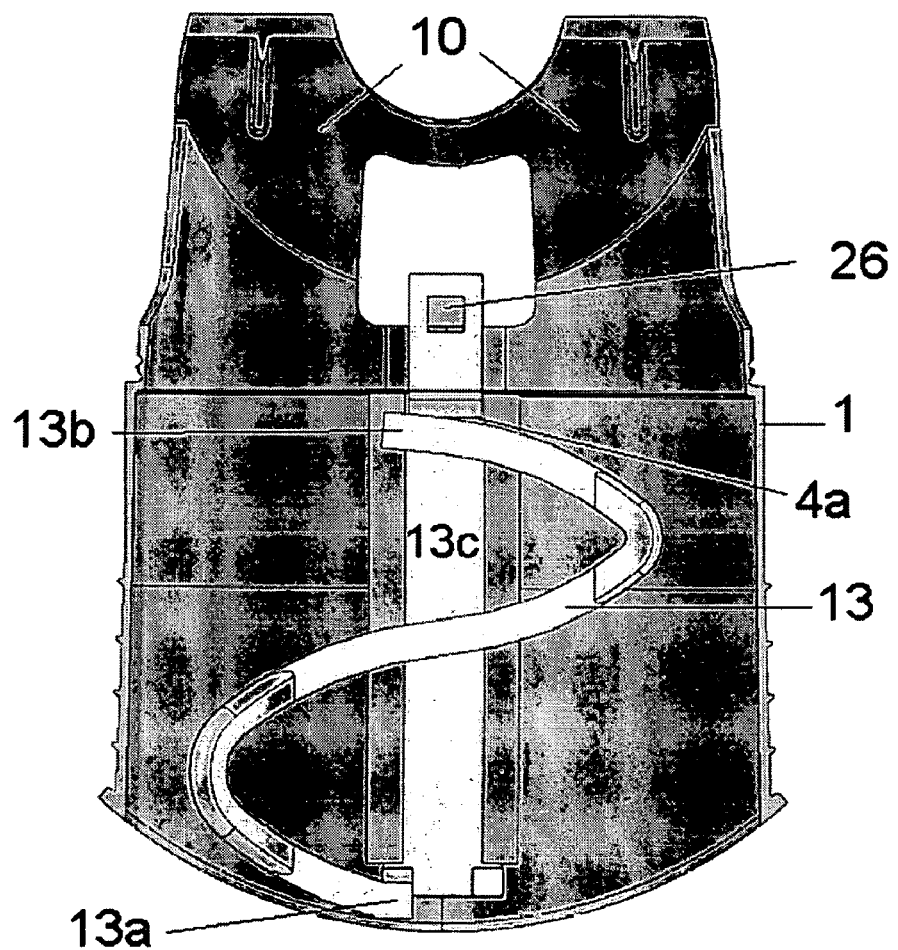
FIG. 14 shows a sixth embodiment with an S-formed spring unit seen from above.
Figure 16A:
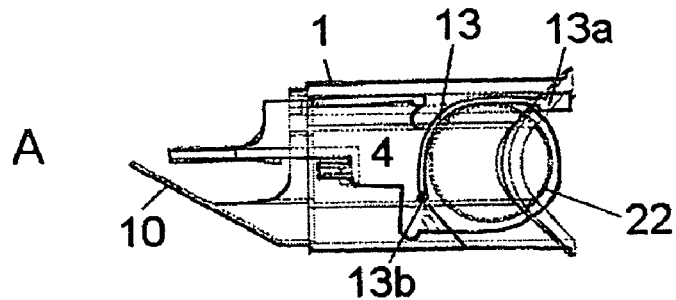
FIGS. 16A-D show an eighth embodiment with a flat spring in A: a forward position seen from the side, B: a forward position seen from the behind, C: a retracted position seen from the side, D: a retracted position seen from above.
Figure 16B:
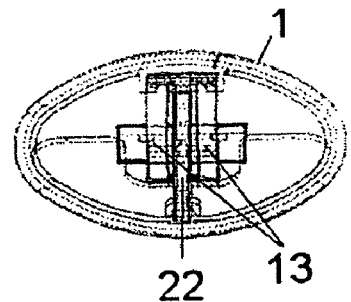
Figure 16C:
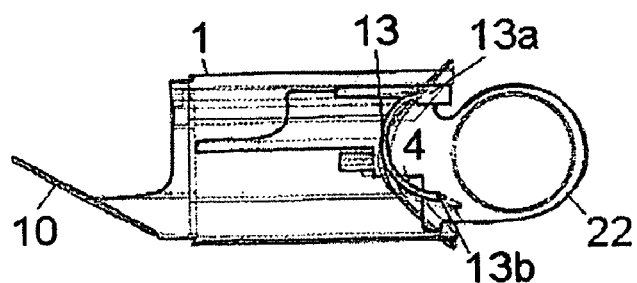
Figure 16D:
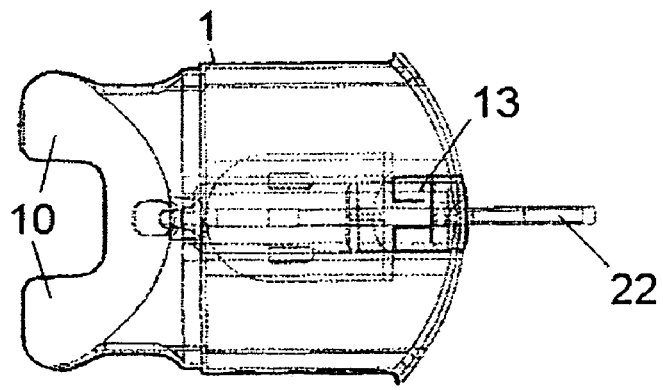
Figure 18A:
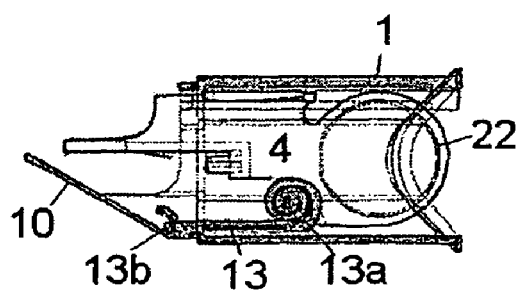
FIGS. 18A-D show a tenth embodiment of the inserter with a spiral spring unit; (A) a forward position seen from the side, (B) a retracted position seen from the side, (C) a forward position seen from above, (D) a retracted position seen from above.
Figure 18B:
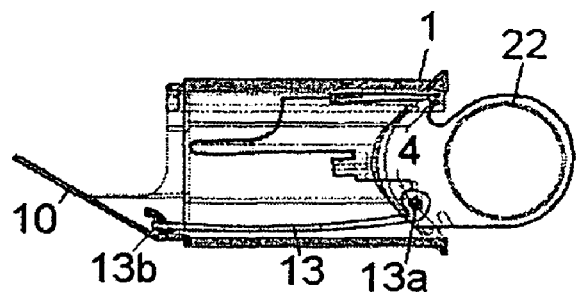
Figure 18C:
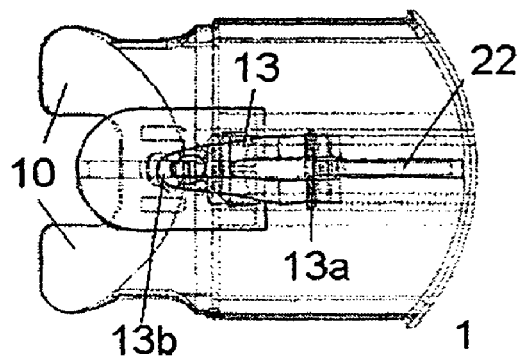
Figure 18D:
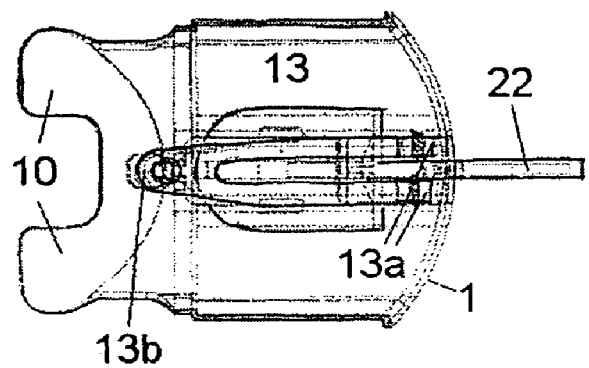

FIG. 14 shows a sixth embodiment with a spring unit 13 formed as an S and constituted of a flat spring made of metal or plastic. The front part 13b of the S-formed spring is fastened to or rests against a surface 4a of the needle unit preferably in a slightly biased state when the needle unit 2, 4 is in its foremost position; the rearmost end of the S-formed spring is fastened to the bottom of the set housing 1. Preferably the rearmost end is fastened to the housing by a prolonged part 13c which can be placed in a trail formed by two opposite and inward turned, upright L-profiles, fastened at the rear end e.g. by a protruding part 25 of the spring unit 13 being pressed into an opening in the set housing 1, and at the front by a three-sided rectangular slit 26 in the prolonged part forming a cut-out which can catch the front edge of the set housing 1. When the handle and the needle unit are pulled back the two ends of the S are pressed together biasing the spring, and when the release button is activated the spring pushes the needle unit 2, 4 forward.

The spring unit 13 according to the sixth embodiment could also be formed as the number 8, have more curves than an ordinary S or more circles than the number 8.

FIGS. 15A and 15B show a seventh embodiment of the inserter where the spring unit 13 is formed of a coiled spring. The rearmost part 13a of the coiled spring unit 13 is stationary to the set housing 1 and the front part 13b of the coiled spring 13 is fastened to the needle unit 2, 4 or to the handle 22 or is simply resting against a part of the movable needle unit or handle in a slightly biased state. The spring unit 13 might be partly enclosed in a trail lying along the bottom wall of the set housing 1. Such a trail would preferably be made of the same material as the set housing 1. The trail can consist of to walls rising from the bottom wall of the set housing 1, and the walls might be parallel, rounded inwards or inclined toward each other. A part of the needle unit 2, 4 is formed as reaching downwards, and this part reaches down into and slides inside the trail. The front end 13b of the spring unit 13 is fastened to or rest against this part. When the handle 22 is brought to the retracted position, this part will assure that the spring unit 13 inside the trail is biased by pushing the movable end 13b of the spring unit 13 towards the stationary end 13a.

FIGS. 16A-16D show an eighth embodiment of the inserter where the spring unit 13 is a circular or rectangular leaf spring. The back end 13a of this flat spring 13 is stationary to the set housing 1, and the back end 13b is fastened or rest against a part of the top wall of the set housing 1. The front end 13b is fastened to the lower side of the needle unit 2, 4 e.g. at a position p2 (see FIG. 9A and 9B).

FIGS. 17A-17D show a ninth embodiment of the inserter where the spring unit 13 is fastened to opposite walls of the set housing 1. In FIGS. 17A-17D, the front ends 13b of the spring unit 13 is fastened to the side walls of the set housing 1, and the rearmost part 13a of the spring unit 13 is fastened to or rests against the movable needle unit 2, 4 at a position p3. In this embodiment the spring unit 13 forms a loop around a low part of the needle unit 2, 4, and does not actually touch the position p3 when the spring unit is in an unbiased state. When the handle 22 is pulled back biasing the spring unit 13, the loop will be deformed and tightened around the low part of the needle unit 2, 4, and when the release button is activated the needle unit 2, 4 will be pulled forward by the spring unit 13 as the loop will return to its original form. Preferably this embodiment would be made of a metal wire or another material with similar characteristics.

It would also be possible to construct the spring unit 13 of a flat spring where the foremost part is resting against the position p3 and indicated in FIG. 17C and 17D with a thin black line, and the rearmost part is fastened to the side walls of the set housing 1 at the rear position of the side walls. In this case the flat spring could be made of metal or plastic.

FIGS. 18A-18D show an inserter with a spiral spring 13 where one end 13a of the spring is fixed to a bottom part of the needle unit 2, 4, and the other end 13b is fixed to a hook or similar at the front part of the set housing 1. When retracting the needle unit 2, 4 the spiral spring is uncoiled, and when releasing the retainer the spring coils up and moves forward, causing the needle and cannula to pierce the skin at a proper angle and enter into the subcutaneous layer at a proper distance.

A tension spring could be made into a compression spring by passing both spring wire ends through the centre of the coils/turns of the spring to the opposite end of the spring. When pulling the wire ends the spring will compress.

Figure 19:
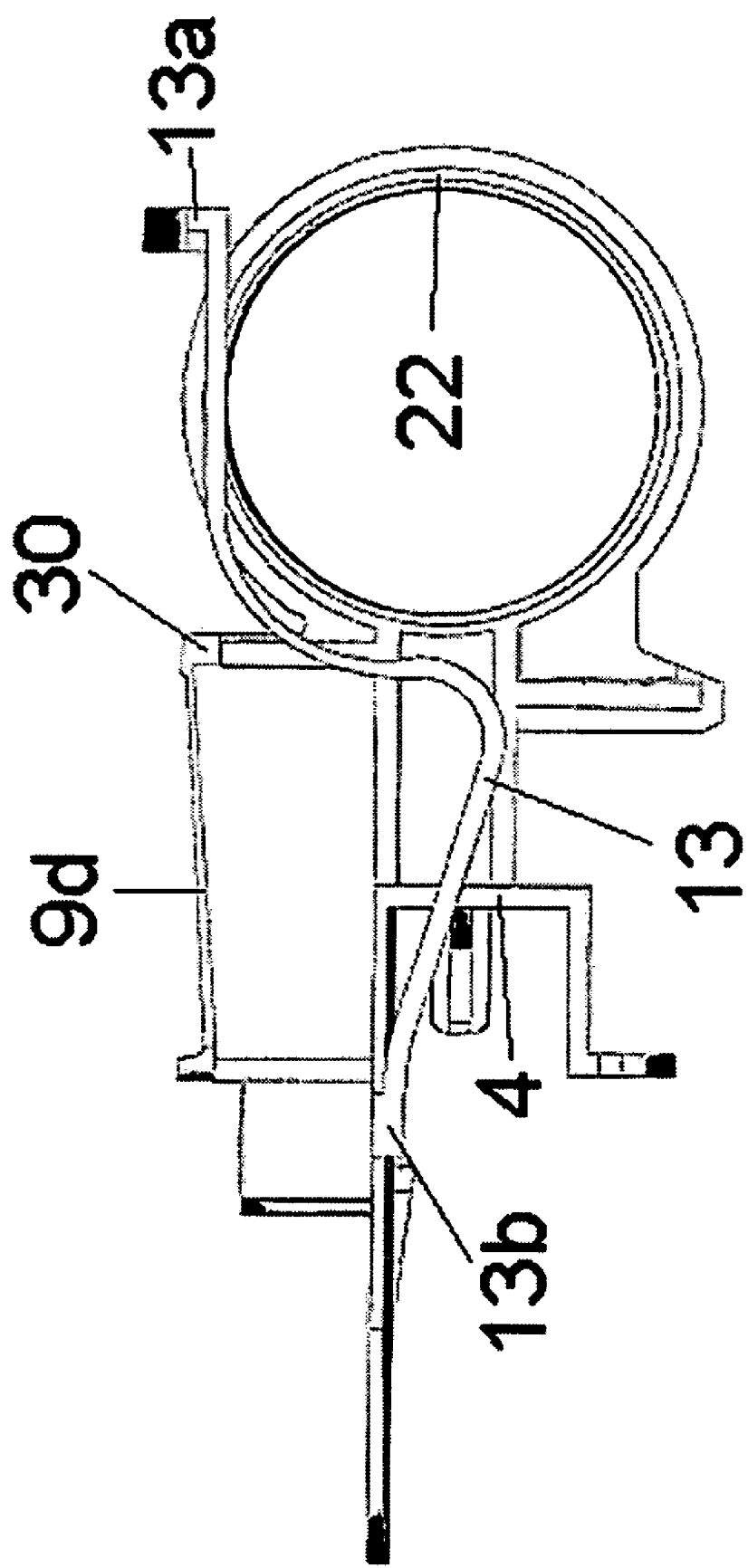
FIG. 19 shows a side view of an eleventh embodiment of an S-formed spring unit.
Figure 20:
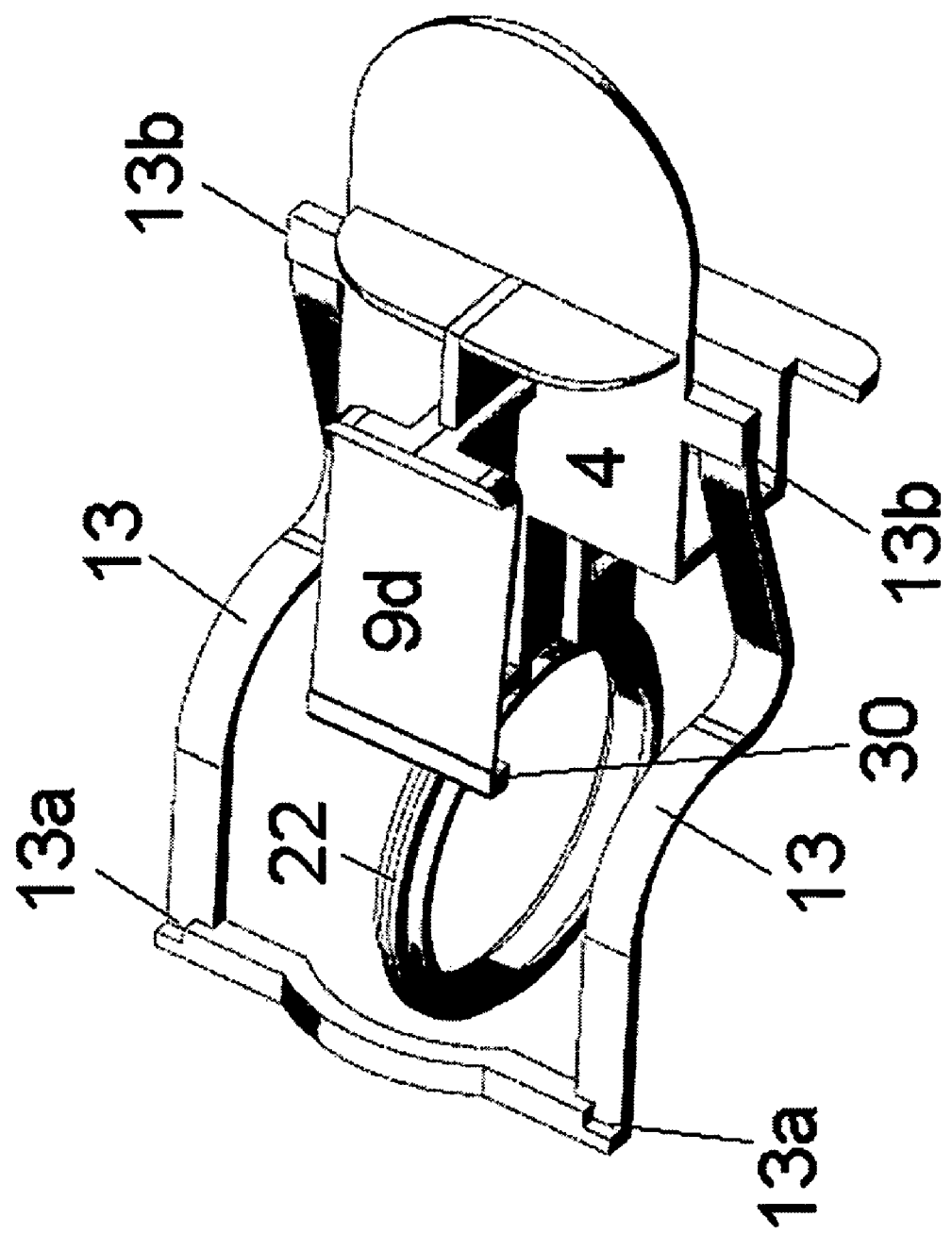
FIG. 20 shows a view from above of the eleventh embodiment of the S-formed spring unit.

In FIG. 19 and 20 is shown an eleventh embodiment the spring unit 13 is made of two flat springs and each of them is formed as a slightly bent S. That the flat springs are formed as an S means that they comprise two convex curves. The flat springs 13 are fastened to the top wall of the set housing 1 in such a way that the back end 13a of the S-formed spring units 13 are stationary in relation to the set housing 1. The front ends 13b of the flat springs are fastened to the needle unit 2, 4. In this embodiment the S-formed spring units 13 are placed between the front end of the needle unit 2, 4 and the back end of the set housing 1 and when the handle 22 is pulled back, the spring units 13 are biased, the two ends of the S-formed spring units, 13a and 13b, are brought closer together. When the release button 17 is activated the spring units 13 will return to the unbiased form and the needle unit 2, 4 will be pushed forward.

FIGS. 21A and 21B show an infusions set which can be inserted with the inserter of the invention. The infusion set comprises an infusion part which will be inserted with the inserter and a connector part which after insertion can form the connection between e.g. an insulin pump and the infusion part. In this embodiment the connector part is symmetrical around the plane formed by the two arms.

Most of the embodiments of the spring unit shown here are compression springs, except the third embodiment which is provided with a spring unit constituted by an elastic O-ring and the tenth embodiment which is provided with a spring unit constituted by a flat spiral spring; these units are tension springs. The ninth embodiment which is constituted by a round thread works both as a compression and tension spring.

Spring units can e.g. be made of steel and in plastic. Spring units in plastic would preferably be made of POM (Polyoxymethylene), and set housing, hard case top and carrier body would preferably be made of PP (Polypropylene). If the spring unit and the carrier body are molded together as one unit the preferred material would be POM.

In this description the expression "flat spring" comprises "leaf spring".

In stead of using a spring unit 13 to bring the needle unit 2, 4 from a retracted to a forward position it would be possible to use magnets. When using magnets repulsive magnets with an adequate repulsive force to move the needle unit 2, 4 from a retracted to a forward position should be chosen. One magnet is placed in the set housing 1 and another magnet is placed at the needle unit 2, 4 carrying the infusion device. The repulsion between the magnets will force the needle unit 2, 4 in a forward direction when releasing the needle unit 2, 4 by activating a release button. The magnets can be molded into the set housing and into the needle unit respectively in order to protect and hide the magnets. Further the repulsive magnets should be made in different sizes in order to avoid that the magnetic field changes.

FIG. 21B shows an infusion set comprising a connector part 40 and cannula housing 3. The cannula housing 3 can be inserted with the inserter according to the claims. After insertion the insertion needle 6 of the inserter is removed together with the inserter and the connector part 40 is placed in the shown position. In this embodiment the connector part 40 is symmetrical around the plane which is parallel to the needle and comprises the two arms 41 of the connector part 40. This connector part 41 also comprises a connector needle 42 which needle penetrates a barrier layer in the cannula housing 3.

The connector part 40 can be connected to a luer coupling member through a not shown tube. Through the luer coupling it is possible to administer a suitable therapeutical substance, such as insulin from a pump. The connector part can also be a sort of closing part with a suitable entrance for an inserting needle of a syringe. Such a closing part can stay in position for up till three days while the user can have medication, e.g. insulin injected through the entrance in order to reduce trauma to the skin caused by repeated penetration of the skin.

The invention claimed is:

1. An inserter for an angled infusion set; the inserter comprising:

a set housing provided with first guiding means on an internal surface for guiding the movement of a carrier body, the carrier body is provided with second guiding means on an external surface for guiding the movement relative to the set housing between a retracted and an advanced position;

a cannula housing comprising a soft cannula to be placed subcutaneously, a needle hub comprising an insertion needle for piercing of the skin, the cannula housing and the needle hub are releasably connected to each other, and when they are connected, the insertion needle is adjoined to the cannula, the needle hub and the carrier body are provided with unreleasable interacting locking means;

a spring unit connected to release means and when the release means are activated, the cannula housing, the needle hub and the carrier body are forced by the spring unit to an advanced position where the needle and cannula can be placed subcutaneously; and a projecting portion extending from a lower base of the set housing, the projecting portion forming an angle in relation to an axis extending in a longitudinal direction of the insertion needle indicating the correct insertion angle for the user during insertion, the projecting portion extending across the axis in front of an end of the cannula when the needle hub is in the retracted position such that the projecting portion lifts up at least a portion of a mounting pad relative to the lower base to a position for contacting the skin during insertion.

2. An inserter according to claim 1, wherein the insertion needle is placed inside the cannula.

3. An inserter according to claim 1, wherein the needle hub and the carrier body are created as a single unit.

4. An inserter according to claim 1, wherein the needle hub comprises openings in a part of the needle hub which openings are covered by material of the set housing, and the carrier body is provided with projections corresponding to the openings in the needle hub.

5. An inserter according to claim 1, wherein the needle unit comprising the needle hub and the carrier body can be placed in a retracted position after insertion.

6. An inserter according to claim 1, wherein the inserter further comprises a stopper.

7. An inserter according to claim 6, wherein the stopper comprises at least one end of a track for a flange.

8. The inserter as claimed in claim 1, wherein the set housing forms at least a part of the delivering packing for the inserter.

9. The inserter as claimed in claim 1, wherein the set housing is provided with a hard top.

10. The inserter as claimed in claim 1, wherein the spring unit is fastened to the set housing in a first position and to the carrier body or the needle hub in a second position, and the first position is situated closer to the front end of the set housing than the second position when the spring unit is unbiased.

11. The inserter as claimed in claim 1, wherein the spring unit is an elastic O-ring.

12. The inserter as claimed in claim 1, wherein the spring unit is fastened to the set housing in a first position and fixed to the carrier body or the needle hub in a second position, and the first position is situated closer to the back end of the set housing than the second position when the spring unit is unbiased.

13. The inserter as claimed in claim 1, wherein the spring unit is a flat spring placed between the back end of the set housing and the needle unit.

14. An inserter for an angled infusion set; the inserter comprising:

a set housing made of a single piece of material and provided with first guiding means on an internal surface for guiding the movement of a carrier body, the carrier body is provided with second guiding means on an external surface for guiding the movement relative to the set housing between a retracted and an advanced position;

a cannula housing comprising a soft cannula to be placed subcutaneously, a needle hub comprising an insertion needle for piercing of the skin, the cannula housing and the needle hub are releasably connected to each other, and when they are connected, the insertion needle is adjoined to the cannula, a spring unit connected to release means and when the release means are activated, the cannula housing, the needle hub and the carrier body are forced by the spring unit to an advanced position where the needle and cannula can be placed subcutaneously; and a projecting portion extending from a lower base of the set housing, the projecting portion forming an angle in relation to an axis extending in a longitudinal direction of the insertion needle indicating the correct insertion angle for the user during insertion, the projecting portion extending in front of an end of the cannula when the needle hub is in the retracted position such that the projecting portion lifts up at least a portion of a mounting pad relative to the lower base to a position for contacting the skin during insertion.

15. An inserter according to claim 14, wherein the insertion needle is placed inside the cannula.

16. The inserter as claimed in claim 14, wherein the set housing is U-shaped.

17. The inserter as claimed in claim 16, wherein the lower leg of the U-shape comprises a projecting part forming an angle with a base line below and parallel to the needle.

18. The inserter as claimed in claim 14, wherein the set housing is formed as a piece of pipe with a rounded or polysided profile.

19. Inserter as claimed in claim 14, wherein the set housing forms at least a part of the delivering packing for the inserter.

20. The inserter as claimed in claim 14, wherein the set housing is provided with a hard top.

21. The inserter as claimed in claim 14, wherein the spring unit is fastened to the set housing in a first position and to the carrier body or the needle hub in a second position, and the first position is situated closer to the front end of the set housing than the second position when the spring unit is unbiased.

22. The inserter as claimed in claim 14, wherein the spring unit is an elastic O-ring.

23. The inserter as claimed in claim 14, wherein the spring unit is fastened to the set housing in a first position and fixed to the carrier body or the needle hub in a second position, and the first position is situated closer to the back end of the set housing than the second position when the spring unit is unbiased.

24. The inserter as claimed in claim 14, wherein the spring unit is a flat spring placed between the back end of the set housing and the needle unit.

25. The inserter as claimed in claim 24, wherein the spring unit has the form of two convex curves placed on each side of the needle unit, and that each curve is fixed to the needle unit at one end and to the set housing behind the fixation to the needle unit at the other end in the unbiased state.

* * * * *